US011754563B2

(12) United States Patent
Li et al.

(10) Patent No.: US 11,754,563 B2
(45) Date of Patent: Sep. 12, 2023

(54) POROUS MEMBRANES WITH A POLYMER GRAFTING, METHODS AND USES THEREOF

(71) Applicant: Global Life Sciences Solutions Operations UK Ltd, Sheffield (GB)

(72) Inventors: Bing Li, Clifton Park, NY (US); Brian Christopher Bales, Niskayuna, NY (US); David Roger Moore, Rexford, NY (US); Jason Michael Nichols, Schenectady, NY (US); Cathryn Ellen Olsen, Wilton, NY (US); William Christopher Alberts, Saratoga Springs, NY (US); Frank John Mondello, Niskayuna, NY (US)

(73) Assignee: GLOBAL LIFE SCIENCES SOLUTIONS OPERATIONS UK LTD, Sheffield (GB)

( * ) Notice: Subject to any disclaimer, the term of this patent is extended or adjusted under 35 U.S.C. 154(b) by 1089 days.

(21) Appl. No.: 14/548,383

(22) Filed: Nov. 20, 2014

(65) Prior Publication Data

US 2016/0146802 A1   May 26, 2016

(51) Int. Cl.
*G01N 33/543* (2006.01)
*G01N 33/548* (2006.01)

(52) U.S. Cl.
CPC ..... *G01N 33/54388* (2021.08); *G01N 33/548* (2013.01); *G01N 33/54353* (2013.01)

(58) Field of Classification Search
CPC ....... G01N 33/54353; G01N 33/54386; G01N 33/548; G01N 33/558
See application file for complete search history.

(56) References Cited

U.S. PATENT DOCUMENTS

| | | | | |
|---|---|---|---|---|
| 4,217,338 A * | 8/1980 | Quash | ................... | C12N 11/06 436/531 |
| 4,363,874 A * | 12/1982 | Greenquist | .......... | G01N 33/525 422/423 |
| 5,453,467 A | 9/1995 | Bamford et al. | | |
| 5,459,080 A | 10/1995 | Adamczyk et al. | | |
| 5,611,995 A * | 3/1997 | de Zoeten | ............. | B01L 3/5023 422/412 |
| 6,372,813 B1 * | 4/2002 | Johnson | ........... | G01N 33/54353 435/174 |
| 6,844,028 B2 | 1/2005 | Mao et al. | | |
| 6,884,628 B2 | 4/2005 | Hubbell et al. | | |
| 7,067,194 B2 | 6/2006 | Mao et al. | | |
| 7,501,157 B2 | 3/2009 | Mao et al. | | |
| 7,629,029 B2 | 12/2009 | Mao et al. | | |
| 7,717,273 B2 | 5/2010 | Kozlov et al. | | |
| 8,178,602 B2 | 5/2012 | Mao et al. | | |
| 9,874,556 B2 * | 1/2018 | O'Farrell | ............. | B01L 3/5023 |
| 2002/0115062 A1 * | 8/2002 | Fletcher | ........... | G01N 33/54386 435/5 |
| 2003/0170474 A1 | 9/2003 | Qiao et al. | | |
| 2004/0076593 A1 | 4/2004 | Bernard et al. | | |
| 2005/0277143 A1 * | 12/2005 | Baggio | ................. | B82Y 30/00 435/6.12 |
| 2006/0008847 A1 * | 1/2006 | Ramel | ................... | B01L 3/5023 435/7.1 |
| 2006/0069213 A1 | 3/2006 | Inaba et al. | | |
| 2006/0078997 A1 * | 4/2006 | Lugade | ............... | G01N 21/645 436/56 |
| 2012/0052006 A1 * | 3/2012 | Boyes | ................. | A61K 33/242 424/1.29 |
| 2012/0288717 A1 | 11/2012 | Mao et al. | | |
| 2013/0171026 A1 | 7/2013 | Li et al. | | |
| 2013/0171368 A1 | 7/2013 | Li et al. | | |
| 2013/0171618 A1 | 7/2013 | Li et al. | | |
| 2013/0171619 A1 | 7/2013 | Li et al. | | |
| 2013/0171669 A1 | 7/2013 | Li et al. | | |
| 2013/0177976 A1 * | 7/2013 | Wang | ...................... | C08B 31/00 435/320.1 |
| 2014/0031291 A1 * | 1/2014 | Mohler | ............... | C12Q 1/6883 514/12.4 |

(Continued)

FOREIGN PATENT DOCUMENTS

| | | |
|---|---|---|
| EP | 1092979 A2 | 4/2001 |
| WO | 2013101855 A1 | 7/2013 |

OTHER PUBLICATIONS

Nagatsugi et al., "Selective Cross-Linking to the Adenine of the TA Interrupting Site within the Triple Helix". Bioorganic & Medicinal Chemistry Letters, (2002) vol. 12, pp. 487-489.*
Bhattacharya et al.,"Grafting: a versatile means to modify polymers: Techniques, factors and applications", Progress in Polymer Science, ScienceDirect, Aug. 2004, vol. 29, Issue 8, pp. 767-814.
Roy et al.,"Cellulose modification by polymer grafting: a review", Chemical Society Reviews, Royal society of chemistry, 2009, Issue 7, 38, 2046-2064.
Zapata et al., "Engineering linear F(ab')2 fragments for efficient production in *Escherichia coli* and enhanced antiproliferative activity," Protein Engineering, vol. No. 8, Issue No. 10, pp. 1057-1062, 1995.
International Search Report and Written Opinion issued in connection with related Application No. PCT/EP2015/076943 dated Apr. 20, 2016.

(Continued)

*Primary Examiner* — Shafiqul Haq
*Assistant Examiner* — Nam P Nguyen
(74) *Attorney, Agent, or Firm* — Eversheds Sutherland (US) LLP

(57) ABSTRACT

A device comprising a modified porous membrane is provided. The modified porous membrane comprises a polymer coating grafted to a porous membrane. The device is used for analyte detection from a biological sample using an immunoassay. The device comprises a sample application zone at one end of the device for applying a biological sample comprising a target analyte; and a detection zone present at another end of the device, downstream of the sample application zone for detecting the target analyte, wherein the detection zone comprises one or more first biomolecules immobilized on a modified porous membrane having a structure of Formula (I).

13 Claims, 9 Drawing Sheets

(56) References Cited

U.S. PATENT DOCUMENTS

2015/0151298 A1* 6/2015 Hobbs ............... B01L 3/502761
　　　　　　　　　　　　　　　　　　　　　　435/7.1
2016/0146795 A1　5/2016 Li et al.
2018/0038854 A1* 2/2018 Choi ................ B01L 3/502761

OTHER PUBLICATIONS

International Search Report and Written Opinion issued in connection with corresponding Application No. PCT/EP2015/076945 dated May 10, 2016.

* cited by examiner

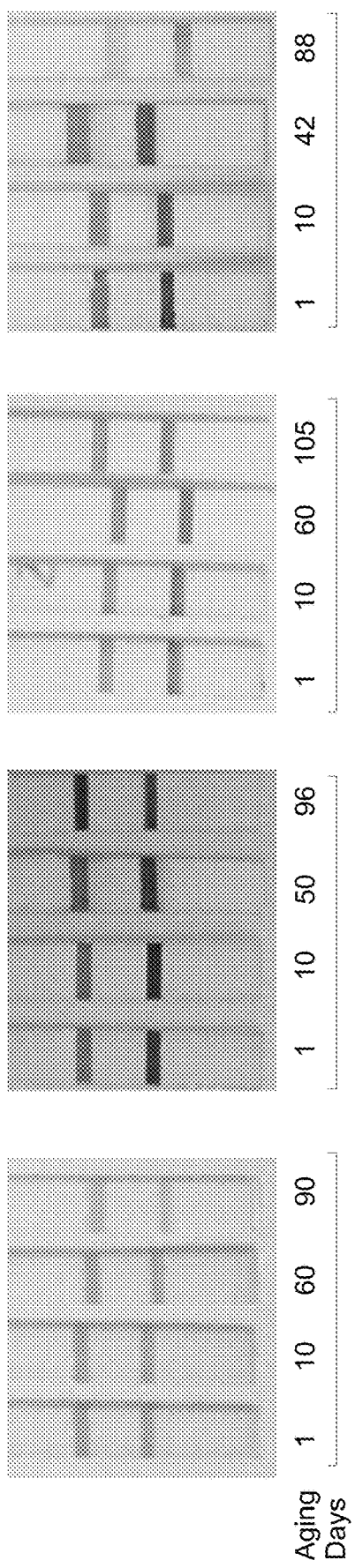
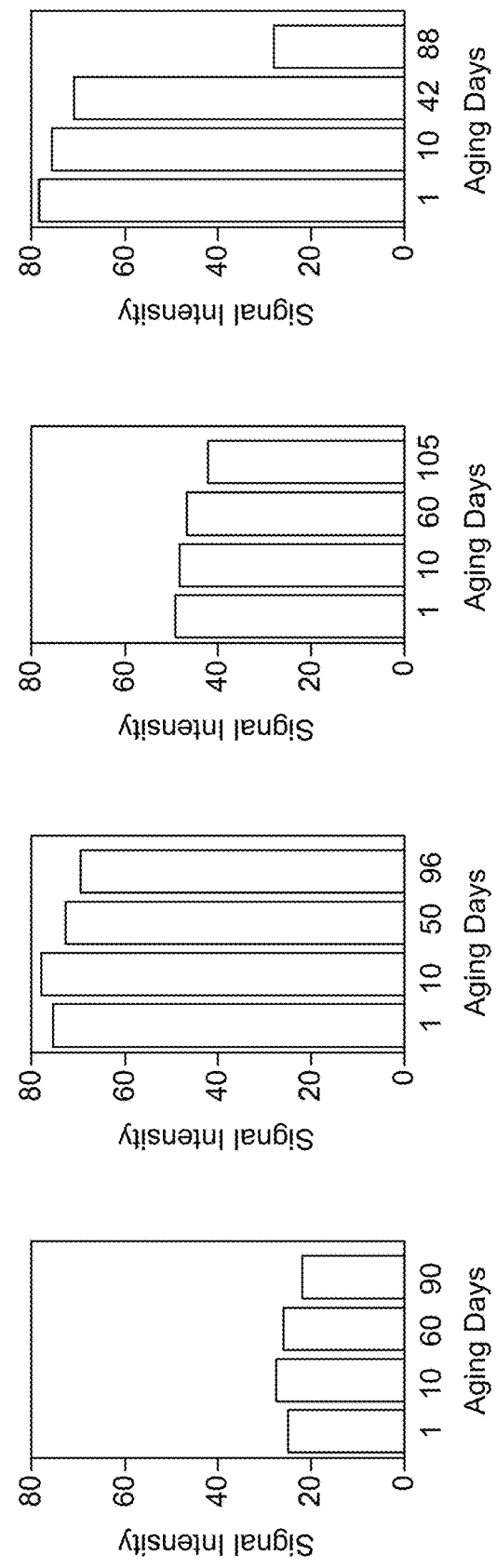

2 min
20 min
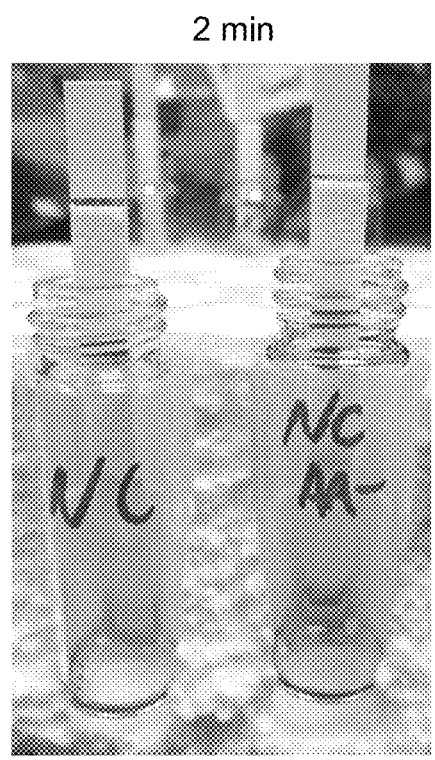
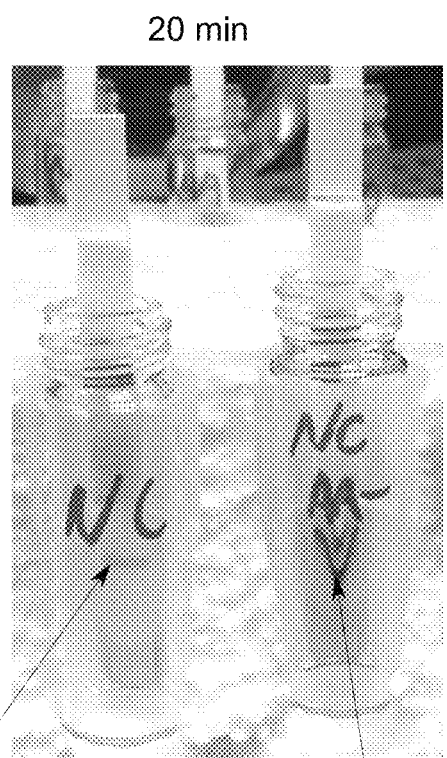
Control line
Accumulation of gold particles on the membrane
FIG. 7A
FIG. 7B

POROUS MEMBRANES WITH A POLYMER GRAFTING, METHODS AND USES THEREOF

FIELD OF THE INVENTION

The present invention generally relates to a device comprising porous membranes grafted with a polymeric coating to facilitate the immobilization of a biomolecule on the porous membrane. Methods of preparing and using the modified porous membranes with these polymeric coatings are also described.

BACKGROUND

Porous membranes, such as nitrocellulose membranes, are routinely used in a variety of processes, including biological applications that require the immobilization of one or more biomolecules. These biomolecules include but are not limited to proteins (e.g., antibodies) and nucleic acids (e.g., deoxyribonucleic acid (DNA) and ribonucleic acid (RNA)). Membranes are needed for the immobilization of biomolecules for use in, for example, immunoassays, in vitro diagnostic tests, particularly point-of-care diagnostic methods, and separation of analytes or biomolecules in biological samples (e.g., blood, urine, saliva, sputum, other bodily secretions, cells, and tissue samples) for a variety of biological processes and medical techniques.

Nitrocellulose membranes exhibit an essentially non-specific interaction between the nitrocellulose membrane and biomolecule(s), and researchers have traditionally relied upon this passive association as the basis for the use of nitrocellulose membranes in a variety of "entrapment" type immobilization methods. Reliance on this passive interaction between the nitrocellulose membrane and a biomolecule of interest, however, may lead to complications for successfully using nitrocellulose membranes in many biological applications because it necessarily limits the amount of the biomolecule that can be immobilized on the nitrocellulose membrane. Dependence on this passive binding process is sufficient for certain applications in which an analyte or biomolecule is present in a high enough concentration in the biological sample to be analyzed. However, this passive binding process limits traditional nitrocellulose membrane-based techniques, for example, in disease states in which the analyte or biomolecule quantity is low and possibly "undetectable" by known compositions and standard methodologies. The passive interaction between the nitrocellulose membrane and the biomolecules of interest may further lead to a degree of detachment of the biomolecules from the nitrocellulose membrane during use in a flow based assay, such as a lateral flow assay. The biomolecules may be detached when a liquid is flowed through the membrane either for washing, elution or detection. This results in a loss of sensitivity for binding analytes by the biomolecules, and increases the cost as more biomolecules need to be used in the binding assay to account for biomolecule detachment in different applications.

Previous research has utilized various techniques to modify porous membranes, for example, nitrocellulose membranes, to improve binding or immobilization of biomolecules on porous membrane substrates. Methods to promote binding of biomolecules to porous membranes, include but are not limited to, ammonia plasma treatment, oxygen plasma treatment, covalent bonding of "bridging" molecules, and hydroxylamine treatment of nitrocellulose membranes. These techniques and membrane modifications have not achieved the desired goals of those of skill in the art.

Therefore, the substrates which are capable of better immobilization and binding of the biomolecules and the methods of modifying (e.g., chemically modifying) the substrate (such as porous membranes) to improve immobilization and binding of biomolecules (e.g., proteins and nucleic acids) of interest are needed in the art.

BRIEF DESCRIPTION

In one embodiment, a device comprises a sample application zone at one end of the device for applying a biological sample comprising a target analyte; and a detection zone present at another end of the device, downstream of the sample application zone for detecting the target analyte, wherein the detection zone comprises one or more first biomolecules immobilized on a modified porous membrane having a structure of Formula (I):

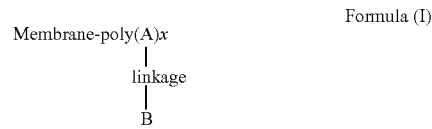

Formula (I)

wherein A is an electron beam (e-beam) reactive moiety, poly $(A)_x$ is a polymer of the e-beam reactive moiety and x is a number of A monomers present in the poly $(A)_x$ polymer; wherein B is a reactive group selected from maleimide, iodoacetate, bromide, N-hydroxysuccinimide-ester (NHS-ester), anhydride, sulfide, carboxylic acid, aldehyde, or combinations thereof; wherein the linkage forms a bond between the poly $(A)_x$ polymer and the B, and wherein the poly$(A)_x$-linkage-B is a polymer coating covalently grafted to the porous membrane; and wherein the device is configured to flow the biological sample along a length of the device from the sample application zone to the detection zone.

In another embodiment, a device comprises a sample application zone at one end of the device for applying a biological sample comprising a target analyte; and a detection zone present at another end of the device, downstream of the sample application zone for detecting the target analyte, wherein the detection zone comprises one or more antibody immobilized on a modified porous nitrocellulose membrane having a structure of Formula (I):

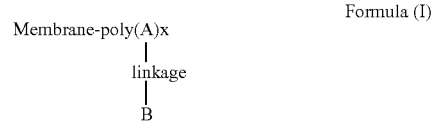

Formula (I)

wherein A is an electron beam (e-beam) reactive moiety, poly $(A)_x$ is a polymer of the e-beam reactive moiety and x is a number of A monomers present in the poly $(A)_x$ polymer; wherein B is a reactive group selected from maleimide, iodoacetate, bromide, N-hydroxysuccinimide-ester (NHS-ester), anhydride, sulfide, carboxylic acid, aldehyde, or combinations thereof; wherein the linkage forms a bond between the poly $(A)_x$ polymer and the B, and wherein the poly$(A)_x$-linkage-B is a polymer coating covalently grafted to the porous membrane; wherein the device is configured to flow the biological sample along a length of the device from the sample application zone to the detection zone and the analytes are detected by capturing by the antibody.

DRAWINGS

FIG. 1 provides a lateral flow strip device structure for detection of various analytes.

FIG. 2A is a schematic representation of the mechanism of grafting on a porous membrane by e-beam irradiation.

FIG. 2B provides ATR FTIR spectra showing grafting efficiency of the various groups onto nitrocellulose membranes in accordance with exemplary methods of the invention.

FIG. 4A provides a LFA test performance of HCG using unmodified FF80HP nitrocellulose membranes aged at room temperature and 50% relative humidity (RH) for the analyte HCG (1000 mIU/ml).

FIG. 4B provides a test performance of HCG using NHS-ester grafted membranes aged at room temperature and 50% RH for the analyte HCG (1000 mIU/ml).

FIG. 4C provides LFA test performance of HCG using epoxide-grafted membranes aged at room temperature and 50% RH for the analyte HCG (1000 mIU/ml).

FIG. 4D provides a test performance of HCG using maleimide grafted modified membranes aged at room temperature and 50% relative humidity (RH) for the analyte HCG (1000 mIU/ml).

FIG. 4E is a graph showing signal intensities of LFA performance of FIG. 4A.

FIG. 4F a graph showing signal intensities of LFA performance of FIG. 4B.

FIG. 4G a graph showing signal intensities of LFA performance of FIG. 4C.

FIG. 4H a graph showing signal intensities of LFA performance of FIG. 4D.

Figure 5:
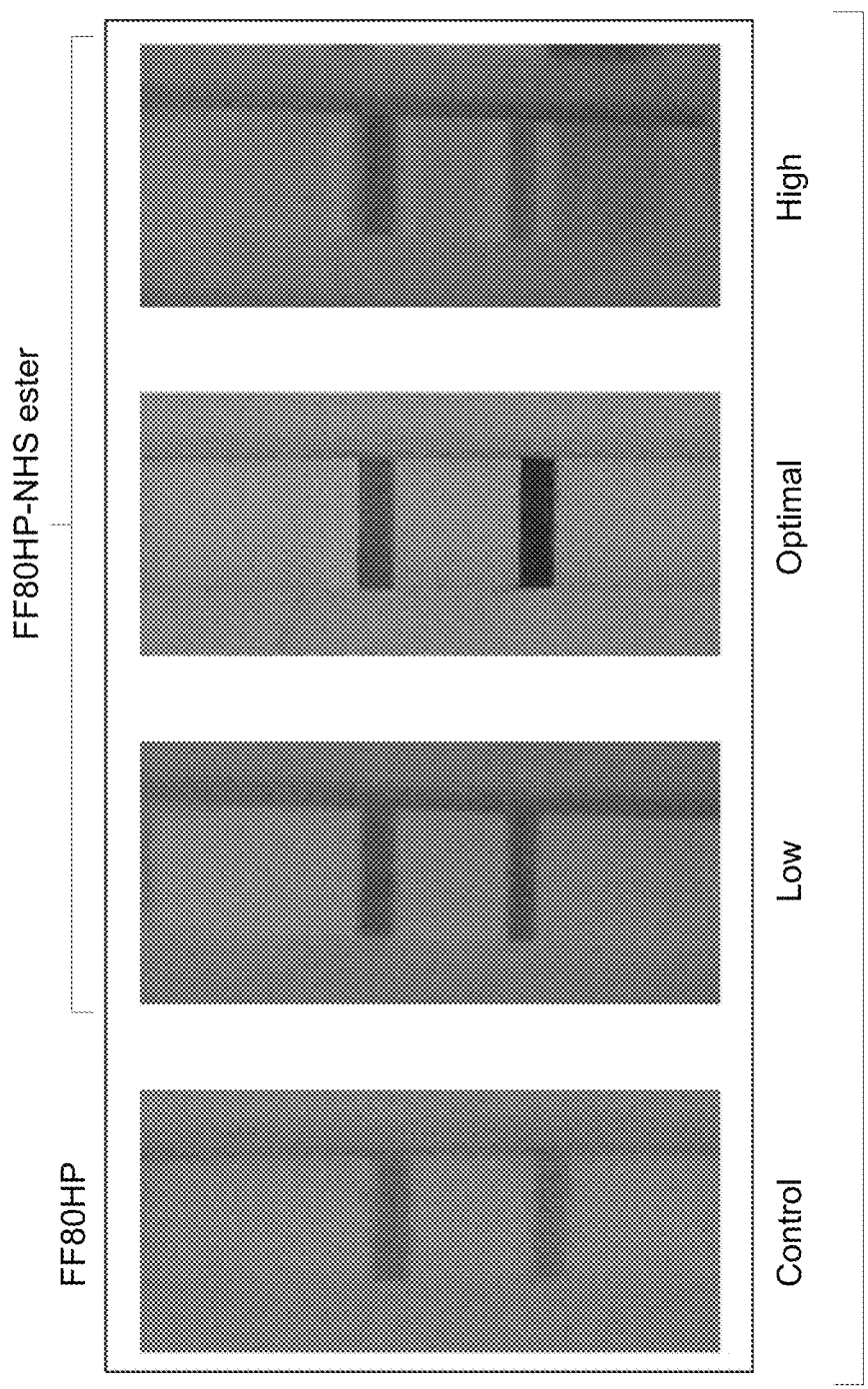

FIG. 5 provides a LFA test performance of HCG using nitrocellulose (NC) grafted with various quantities of NHS-ester functionality.

Figure 6:
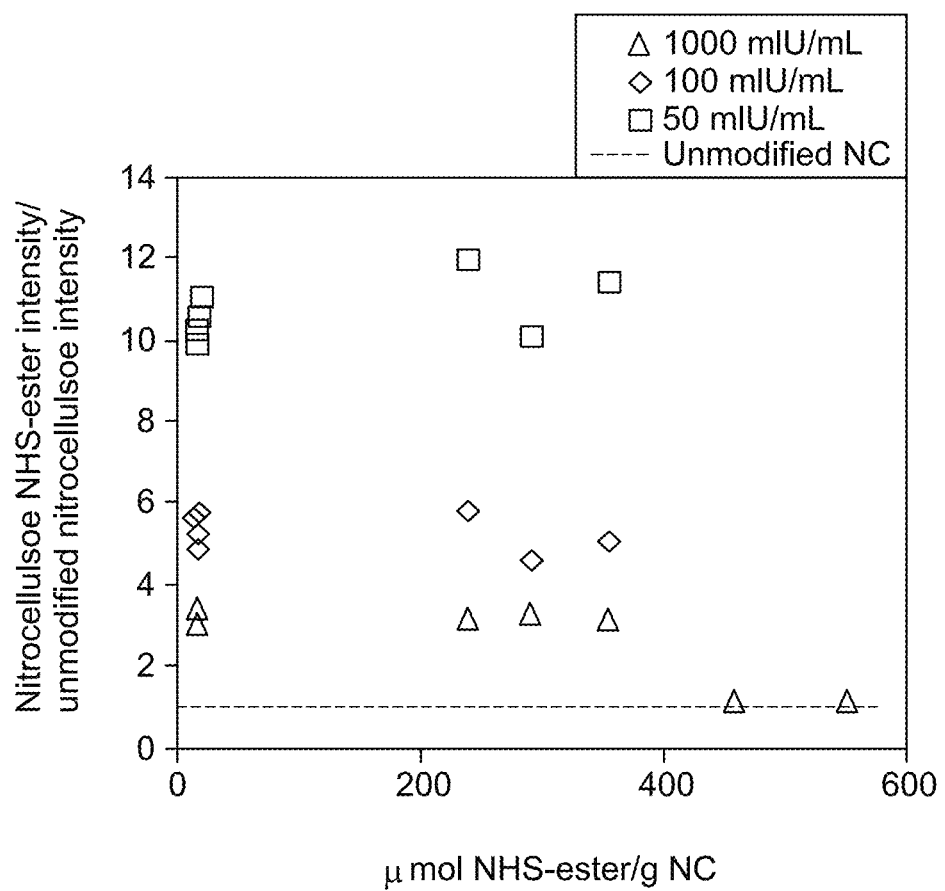

FIG. 6 is a graph showing improvement in the background corrected test line intensity when compared to unmodified FF80HP nitrocellulose as a function of the quantity of NHS-ester grafted on nitrocellulose.

FIG. 7A provides LFA test performance of acrylic acid grafted nitrocellulose (NC-AA) after 2 mins (t=2 mins), wherein NC-AA is the hydrolysis product of nitrocellulose grafted with 2,5-dioxopyrrolidin-1-yl acrylate (NC-NHS-ester).

FIG. 7B provides LFA test performance of acrylic acid grafted nitrocellulose (NC-AA) after 20 mins (t=20 mins), wherein NC-AA is the hydrolysis product of nitrocellulose grafted with 2,5-dioxopyrrolidin-1-yl acrylate (NC-NHS-ester).

Figure 8A:
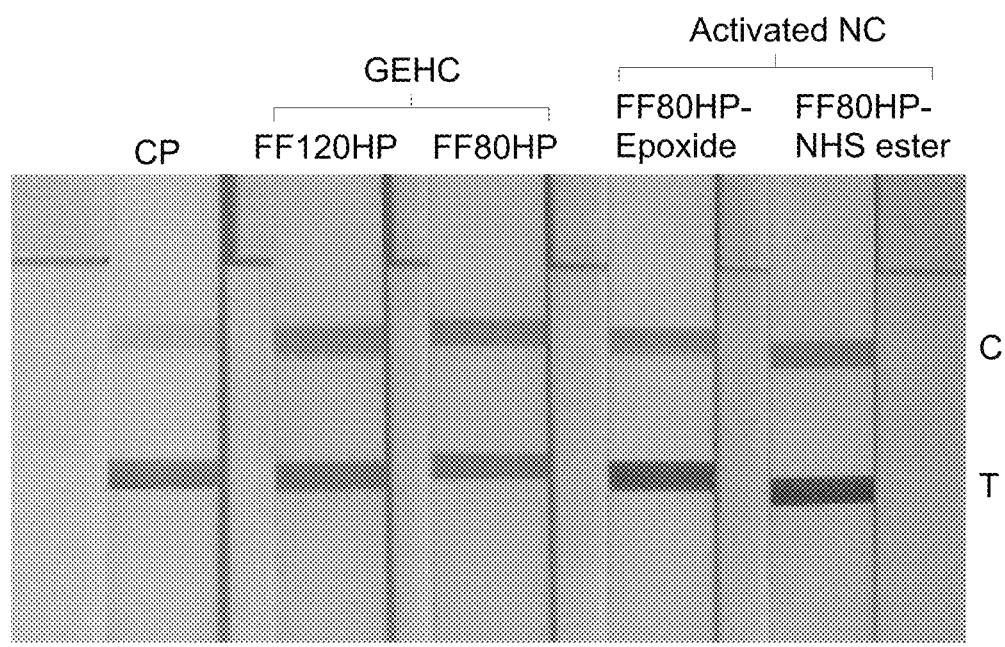

FIG. 8A provides a comparison of LFA performance of HCG using activated nitrocellulose membranes of the present invention, unmodified FF80HP NC membrane, and commercially available nitrocellulose membranes.

Figure 8B:
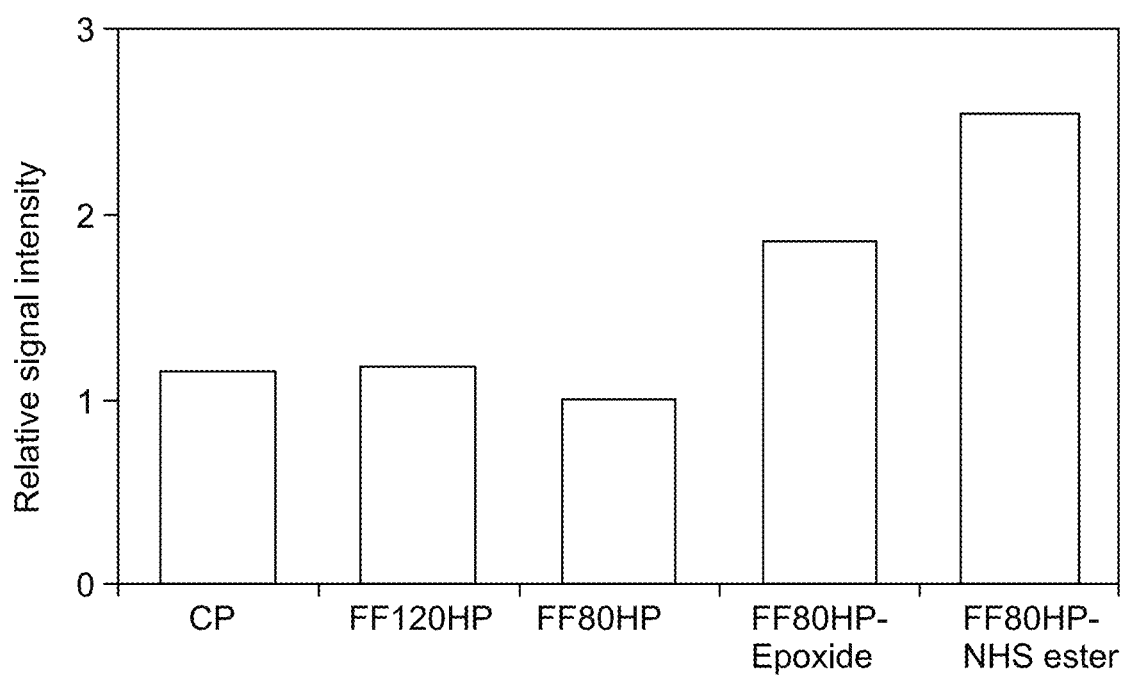

FIG. 8B is a graph showing a comparison of signal intensities of LFA performance of HCG using activated nitrocellulose membranes of the present invention, unmodified FF80HP NC membrane, and commercially available nitrocellulose membranes, normalized against FF80HP.

DETAILED DESCRIPTION

In the following specification and the claims, which follow, reference will be made to a number of terms, which shall be defined to have the following meanings.

The singular forms "a", "an" and "the" include plural referents unless the context clearly dictates otherwise. "Optional" or "optionally" means that the subsequently described event or circumstance may or may not occur, and that the description includes instances where the event occurs and instances where it does not. Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

To more clearly and concisely describe and point out the subject matter of the claimed invention, the following definitions are provided for specific terms, which are used in the following description and in the appended claims. Throughout the specification, exemplification of specific terms should be considered as non-limiting examples.

As used herein, the term "nitrocellulose membranes" includes porous membrane products containing any nitrogen concentration, a diversity of pore sizes, and variable membrane thicknesses. In particular embodiments, the pore size of the porous membrane may be in the range of 0.01 to 50 microns. Moreover, the pore diameter may be uniform throughout the porous membrane or, alternatively, pore diameter may be irregular. It is well within the skill and the knowledge of one in the art to select a porous membrane, such as a nitrocellulose membrane, with the appropriate nitrogen content, pore size, and membrane thickness to achieve a specific, desired result. Moreover, the skilled artisan would immediately understand and appreciate the meaning of the phrase a "nitrocellulose membrane" and that such nitrocellulose membranes, for example, or commercially available nitrocellulose membranes, may be "unbacked" or "unmodified" membranes or alternatively contain a "backing material" or "backing support" such as polyester (PE). The choice as to whether to use an "unbacked" or "backed" porous membrane (e.g., nitrocellulose membrane) is dependent upon the particular application to be performed and is well within the purview of one of ordinary skill in the art to make such a selection.

As used herein, the term "modified", particularly in reference to the disclosed porous membranes and solid phase materials, is intended to include any alteration to a porous membrane or a solid phase material, for example, a chemical alteration, of the original, unmodified porous membrane or solid phase membrane substrate. The porous membranes may be "modified" (e.g., chemically modified) via formation of polymers containing chemical moieties capable of forming covalent bonds with other nucleophilic elements such as nitrogen or sulfur, such as an N-hydroxysuccinimide-ester (NHS-ester) group-containing compound grafted to the porous membrane. In one aspect, the porous membrane is a nitrocellulose membrane comprising polymers of the NHS-ester group-containing compound grafted on the porous membrane. The modified porous membranes may comprise at least one polymer coating grafted to the porous membrane to facilitate immobilization of a biomolecule on the porous membrane. Similarly, the porous membrane may be a nitrocellulose membrane comprising polymers of the NHS-ester, maleimide, iodoacetamide, or bromide group-containing compound or combinations of two or more of these grafted on the porous membrane.

As used herein, the term "N-hydroxysuccinimide ester (NHS-ester) group-containing compound" refers to any chemical compound that comprises at least one NHS-ester group. Any polymerizable NHS-ester group-containing compound, such as 2,5-dioxopyrrolidin-1-yl acrylate, may be used in the compositions and methods of this disclosure. In one embodiment, the modified porous membrane is a nitrocellulose membrane grafted with polymers of 2,5-dioxopyrrolidin-1-yl acrylate.

As used herein, the term "activated membrane" refers to the membrane that comprises one or more of a first biomolecule attached to the modified membranes. The first biomolecules may bind to the modified membrane through a reactive group "B" as referred to compound of structure (I). The "modified membrane" becomes "activated membrane" after the first biomolecules bind to the modified membrane. The "activated membrane" may be interchangeably referred to herein as "activated porous membrane".

As used herein, the term "first biomolecule" refers to biomolecules which bind to the modified membrane surface, wherein the biomolecules may include proteins, peptides or nucleic acids. In a specific embodiment, the first biomolecule is protein, such as antibody. The first biomolecules may immobilize on the modified membrane surface and forms an activated membrane. The activated membrane comprising first biomolecule may further be used for capturing one or more analytes present in a biological sample. In some embodiments, the analytes are biomolecules and the first biomolecules on the activated membrane capture the analytes (biomolecules) of a sample.

As used herein, the term "porous membrane" refers to any membrane that comprises pores and at least a polymer may be grafted therein. The porous membranes, where polymer grafting is feasible, include any commercially available porous membrane, particularly a commercially available nitrocellulose membrane.

As used herein, the term "analyte" refers to a substance or a chemical constituent whose presence or absence in, for example, a biological sample is being determined via an assay or a test, such as an immunoassay or other diagnostic test. In some examples, an antigen present in a biological sample may serve as an analyte, wherein the antigen binds to an antibody immobilized on a substrate during analysis. Non limiting examples of analytes may include human chorionic gonadotropin (hCG), creatine kinase-MB (CK-MB) and Troponin I.

As used herein, the term "anti-analyte" refers to a substance or chemical constituent that has specificity for binding to an analyte molecule. The anti-analyte may help in detection of analyte molecules in different reactions or assays, such as in an immunoassay or other diagnostic test. For detection purpose, the anti-analyte molecules may be tagged with a substrate or fluorophore which generates color or fluorescence or quenches fluorescence on binding to an analyte, such as an antigen. The anti-analyte molecules may be bound to a probe including but not limited to a fluorescence probe, phosphorescence probe, chemical probe, optical probe, etc. For example, if an analyte is an antigen bound to an antibody immobilized on a substrate, then the probe modified anti-analyte may bind to that antigen and provide indication of the analytes presence, via generation of color or fluorescence for detection.

As used herein, the term "biological sample" includes but is not limited to blood, serum, lymph, saliva, mucus, urine, other bodily secretions, cells, and tissue sections obtained from a human or non-human organism. A buffer comprising one or more biomolecules may also be considered as a biological sample.

As used herein, the term "biomolecule" refers without limitation to a nucleic acid (e.g., DNA or RNA) or a protein (e.g., an antibody). The biomolecules further include any organic molecule derived from an organism (e.g., a human patient).

"Immunoassay" is used herein in its broadest sense to include any technique based on the interaction between an antibody and its corresponding antigen. Such assays are based on the unique ability of an antibody to bind with high specificity to one or a very limited group of similar molecules (e.g., antigens). A molecule that binds to an antibody is called an antigen. Immunoassays can be carried out using either the antigen or antibody as the "capture" molecule to "capture" the other member of the antibody-antigen pairing.

Embodiments of the devices comprising modified porous membranes are provided herein, such as devices comprising modified nitrocellulose membranes. The modified membranes may be used in various applications, for example, immunoassays, in vitro diagnostic tests (e.g., point-of-care diagnostic applications) and techniques for the separation of biomolecules of interest in biological samples. The porous membranes having polymer grafting that improve the immobilization and binding of biomolecules to the porous membranes are advantageous over different membranes known in the art.

A device is provided, wherein the device may comprise a solid surface, wherein the solid surface may be coated with a modified nitrocellulose substrate material. The device may further comprise one or more different components for receiving sample, contacting sample with the first biomolecules immobilized on the modified substrate. In some embodiments, the device is used for capturing an analyte present in the sample applied to the device. The device may be used as a lateral flow device for detection of different analytes.

In some embodiments, a device comprises a sample application zone at one end of the device for applying a biological sample comprising a target analyte; and a detection zone present at another end of the device, downstream of the sample application zone for detecting the target analyte. In these embodiments, the detection zone comprises one or more first biomolecules immobilized on a modified porous membrane having a structure of Formula (I):

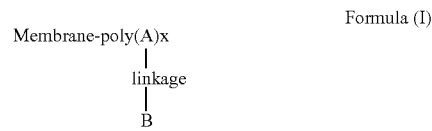

wherein A is an electron beam (e-beam) reactive moiety, poly $(A)_x$ is a polymer of the e-beam reactive moiety and x is a number of A monomers present in the poly $(A)_x$ polymer; wherein B is a reactive group selected from maleimide, iodoacetate, bromide, N-hydroxysuccinimide ester (NHS-ester), anhydride or combinations thereof; wherein the linkage forms a bond between the poly $(A)_x$ polymer and the B, and wherein the poly$(A)_x$-linkage-B is a polymer covalently grafted onto the porous membrane; and wherein the device is configured to flow the biological sample along a length of the device from the sample application zone to the detection zone.

Figure 1:
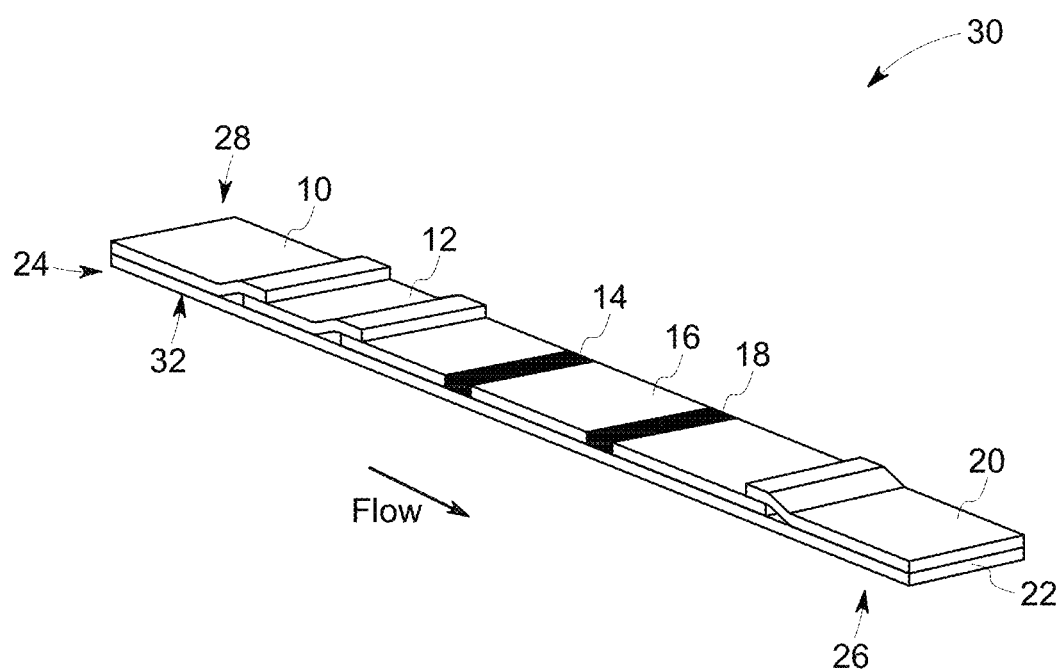

Referring to FIG. 1, one embodiment of a device 30 is represented, wherein the device 30 comprises a longitudinal strip, which encompasses various components. The device comprises a sample pad or sample loading pad 10, followed by a conjugate release pad 12. The sample pad or sample loading pad 10 is an area on the device where sample is applied. In one or more embodiments, the sample loading pad 10 is same as sample application zone. As mentioned a conjugate release pad 12, wherein the conjugate release pad is configured for dry and stable storage of conjugate that is required for detection of analytes. The conjugate is typically an antianalyte probe, such as a secondary antibody which binds to a target analyte, wherein the conjugate is further linked to a reporter, such as a colorimetric reporter (such as gold particles), fluorescence reporter, chemiluminescence reporter or magnetic beads. The conjugate release pad 12 does not retain the conjugate upon rehydration using sample fluid. The modified membrane 16 is the middle portion of the strip wherein a test line 14 and a control line 18 are deposited using any method known in the art, such as inkjet. The sample loading pad 10 and the conjugate release pad 12 are located at one end of the substrate. An absorbent pad 20 is located at the other end of the substrate. The absorbent pad is further known as a wicking pad. The wicking pad or absorbent pad 20 is followed by a backing layer 22. The sample flows through the substrate from sample loading pad 10 to the wicking pad 20.

In some embodiments, the device 30 comprises an activated porous membrane disposed on a solid support. The solid support may be a backing layer 22, as shown in FIG. 1. The solid support may be selected from a microtiter plate, petri plate, a glass slide. In some examples, the solid support 22 may be part of the device 30, wherein the solid support may be coupled to an analytical system. In some other embodiments, the solid support 22 is part of another device, wherein the device may be an analytical device, a detection system, a portable device, a fieldable detection system, or a part of an immune assay kit. In one embodiment, the device 30 is a lateral flow device for immune assay.

In one or more embodiments, the device 30 (a longitudinal strip) comprises a first end 24 and a second end 26, wherein the sample applied to the first end 24 flows towards the second end 26 by lateral flow. In some embodiments, the device 30 further comprises a membrane 28, which is disposed on the sample pad or adjacent to the sample pad for purification of a biological sample, such as blood. The purification membrane 28 may be a filter membrane which provides a primary separation of the biomolecules present in a sample and may help to enrich the sample with the target analytes. In one or more embodiments, the device further comprises a flow controller 32. The flow controller may adjust the flow rate of the sample after applied to the sample application zone, adjacent to the sample pad 10.

In some embodiments the device 30 comprises a modified membrane which may be used for a lateral flow assay. The modified membrane may further comprise one or more first biomolecules immobilized on the modified membrane to form an activated membrane 16, which is used for capturing target analytes present in the biological sample. In one or more embodiments, the first biomolecule comprises an antibody, an aptamer, a nucleic acid or a combination thereof. The lateral flow assay is a common immunoassay, largely due to its ease of use, and includes such products as commercially available home-pregnancy tests and routine drug tests. Lateral flow assays are particularly advantageous because the devices and methods are generally simple to use and to interpret the test results, even by an individual without formal medical training.

Lateral flow devices, such as a device 30 represented in FIG. 1 and methods associated thereof are intended to detect the presence or absence of a target analyte or biomolecule, for example, human chorionic gonadotropin (hCG or HCG) in a lateral flow home pregnancy test, in a biological sample, such as, urine. Although there is variation among lateral flow devices and assays, these tests are commonly used for home testing, point of care testing, and laboratory use.

Lateral flow assays are often presented in a convenient "dipstick" format described further in the examples below, in which the biological sample to be tested flows along a solid substrate (e.g., a porous membrane, often a nitrocellulose membrane) via capillary action. In certain formats of lateral flow assays, the dipstick is immersed in the biological sample, it encounters one or more reagents previously imprinted on the dipstick as the biological sample flows up the test strip, thereby encountering lines or zones, such as test line 14 on the test strip 16 (as shown in FIG. 1) that have been previously imprinted with, for example, an antibody or antigen (e.g., hCG). When the biological sample encounters this reagent(s), a signal is generated to indicate whether the test is positive or negative for the presence of the analyte or biomolecule of interest (e.g., frequently a line visible to the naked eye as in the detection of hCG in a home pregnancy test indicative of the presence of hCG in the patient's urine).

In some embodiments of the device 30, as referring to FIG. 1, the test line 14 may comprise a different antibody, depending on the detection requirement. In one example, for a pregnancy detection kit, the test line 14 comprises an anti-hCG antibody. In this example, an user add a urine sample to the sample loading pad 10, and if the sample is taken from a pregnant woman, a specific antigen is present in the sample which reacts with the antibody impregnated at the test line 14. The sample flows from loading pad 10 present at the first end 24 to the test line 14 on the modified membrane 16 by lateral flow. The sample further flows towards the control line 18 and is transferred to the wicking pad 20 present at the second end 26. The control line 18 typically contains a control line antibody, which binds to a bioconjugate with reporting tag and after binding to the control line antibody, provides a colored line for both a positive and a negative test. The purpose of depositing the control line 18 is to provide an indication to the user that the device has functioned in a correct manner when used for a fluidic sample. If signal is not observed at the control line 18, the test results must be discarded regardless of whether or not signal is observed at the test line 14. In case of a positive pregnancy test, both lines 14 and 18 provide colored lines. In this case, the bioconjugate with reporting tag captures the analyte/antigen from the urine sample of a pregnant woman and provides color at line 18.

In another example of the device 30 (FIG. 1), the test line 14 may comprise an anti-CKMB antibody, which is a cardiac marker and any type of diseased state related to CKMB may be detected using the strip with this marker. In another example, an anti-troponin I antibody may also be used for test line 14, wherein the anti-Troponin I is also a cardiac marker and the strip may be used to detect cardiac disease. In these examples, serum or blood may be used as a sample.

The performance, sensitivity, and specificity of lateral flows assays are significantly improved using the devices, such as a device 30 comprising an activated porous membrane 16 with polymer grafted therein. The concentration of the analyte needed to obtain an accurate test results for immunoassays are also decreased and the time to detect the presence or absence of the analyte or biomolecule is reduced using the lateral flow device comprising the activated membrane, such as a modified nitrocellulose membrane comprising first biomolecules, such as antibody.

The determination and optimization of an appropriate first biomolecule, such as antibody binding and detection techniques is standard and well within the routine capabilities of one of skill in the art. A method of detection of first biomolecule (antibody) binding or immobilization on the modified membrane (such as a polymer grafted nitrocellulose membrane) using the device is provided herein. In some embodiments, the detection of antibody binding may be facilitated by coupling the antibody to a detectable substance or a detection probe, and the examples of detectable substances or probes are described later in detail.

The activated porous membranes 16 of the lateral flow device 30 comprising a polymer grafting of, for example, NHS-ester containing compound may further be modified to comprise a hydrophilic compound immobilized on the porous membrane. The introduction of a hydrophilic compound onto the modified porous membrane comprising a polymer grafting may act as a blocking agent to decrease non-specific, background binding to the porous membrane (e.g., nitrocellulose membrane). In some embodiments, minimizing non-specific binding of the molecules to a modified porous membrane improves the signal to noise ratio in, for example, immunoassays. In these embodiments, the immunoassays are based on the specific interaction of an antibody immobilized on the membrane and a specific biomolecule of interest (e.g., a protein) present in a sample being analyzed for the presence or quantity of this biomolecule.

The device 30 comprising an activated porous membrane 16 may be used for a variety of immunoassays, such as those used for drug testing, hormones, numerous disease-related proteins, tumor protein markers, and protein markers for cardiac injury. The device may also be used for immunoassays to detect antigens on infectious agents such as *Hemophilus, Cryptococcus, Streptococcus,* Hepatitis B virus, HIV, Lyme disease, and *Chlamydia trichomatis*. These immunoassay tests are commonly used to identify patients with these and other diseases. Accordingly, compositions and methods for improving the sensitivity, specificity, and detection limits in immunoassays are of great importance in the field of diagnostic medicine. The device comprising the activated porous membranes may be employed for immunoassays, in vitro diagnostic tests (e.g., point-of-care diagnostic applications) and techniques for the separation of biomolecules of interest in biological samples.

The activated porous membrane of the device may be formed by immobilizing one or more first biomolecules on a modified porous membrane, wherein the modified porous membrane comprises polymer graft on the membrane surface. One or more examples of a modified porous membrane is provided herein, the modified porous membrane has the structure of Formula (I), wherein Formula (I) is:

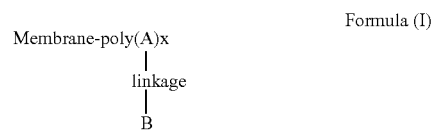

Formula (I)

wherein A is an electron beam (e-beam) reactive moiety, poly $(A)_x$ is a polymer of the e-beam reactive moiety and x is a number of A monomers present in the poly $(A)_x$ polymer; wherein B is a reactive group selected from maleimide, iodoacetate, bromide, N-hydroxysuccinimide ester (NHS-ester), anhydride or combinations thereof; wherein the linkage forms a bond between the poly $(A)_x$ polymer and the B, and wherein the poly$(A)_x$-linkage-B is a polymer covalently grafted onto the porous membrane.

In one or more embodiments, the modified porous membrane is incubated with a first biomolecule, wherein the first biomolecule binds to the modified porous membrane through reaction with the B reactive group to form an activated porous membrane comprising the first biomolecules. The device comprising the activated porous membrane may be used for detecting an analyte present in a biological sample. In this regard, a biological sample may be added to the activated porous membrane of the device. At least one analyte of the biological sample may be detected when the first biomolecule of the activated porous membrane captures the analyte.

A schematic of exemplary modified porous membranes is provided above in Formula (I) comprising a polymer grafted to a porous membrane, wherein the polymer is grafted on the membrane surface. In some embodiments, the grafted polymer comprises: 1) a polymer of a variable length of a chain of monomers of an electron (e-beam) reactive moiety designated as poly$(A)_x$; 2) a functional group labeled B which reacts with specific chemical groups, for example, an amine (when B is a N-hydroxysuccinimide ester), or a thiol (where B is an iodoacetate or maleimide), present on a biomolecule of interest, thereby facilitating immobilization of a biomolecule on the porous membrane through formation of a covalent bond; 3) a linkage that forms a bond between poly$(A)_x$ and group B. The grafted polymer (e.g., labeled "poly$(A)_x$-linkage-B" in the schematic formula) comprises several components (e.g., poly$(A)_x$ polymer, a linkage, and a functional moiety B) and the polymeric coating is grafted (e.g., covalently bond) to the surface of the porous membrane.

As noted, the porous membrane comprises a poly $(A)_x$ polymer of the e-beam reactive moiety group A, wherein x is a number of A monomers present in the poly $(A)_x$ polymer. During the e-beam induced polymerization, the e-beam generates radicals (unpaired electrons) at locations on the porous membrane, the monomer (A) or the growing poly $(A)_x$ polymer. Radicals formed on the porous membrane serve as initiation sites for the growth of the poly $(A)_x$ polymer, leading to grafting of poly $(A)_x$ on the porous membrane. This process is depicted in scheme (I) when the porous membrane is nitrocellulose, wherein ∪ represents the grafting of one polymer to another, x is the number of polymerized monomers, and B is as defined above. In the case where poly$(A)_x$-linkage-B is a copolymer, two or more monomers may be present during the e-beam induced polymerization.

Scheme I:
Polymer grafting on nitrocellulose membrane by e-beam radiation

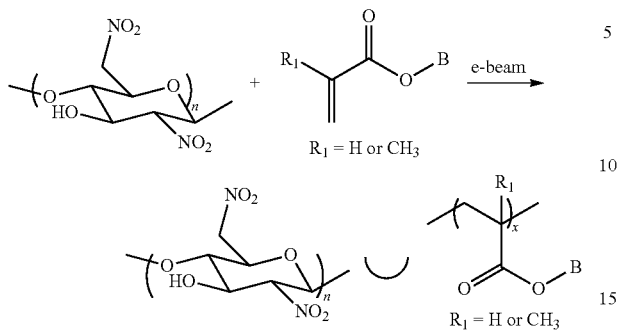

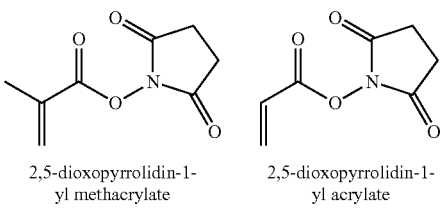

2,5-dioxopyrrolidin-1-yl methacrylate    2,5-dioxopyrrolidin-1-yl acrylate

The examples of maleimides used to form the grafted polymer on the porous substrate may include, but are not limited to:

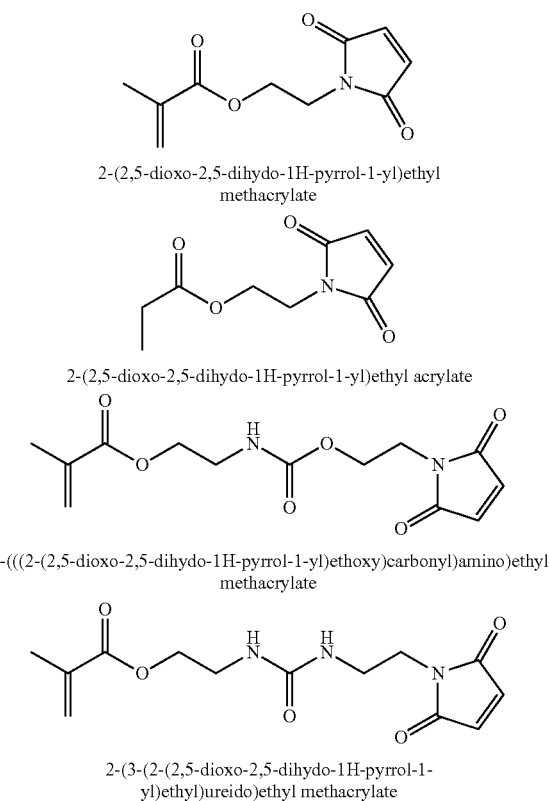

2-(2,5-dioxo-2,5-dihydo-1H-pyrrol-1-yl)ethyl methacrylate 2-(2,5-dioxo-2,5-dihydo-1H-pyrrol-1-yl)ethyl acrylate 2-(((2-(2,5-dioxo-2,5-dihydo-1H-pyrrol-1-yl)ethoxy)carbonyl)amino)ethyl methacrylate 2-(3-(2-(2,5-dioxo-2,5-dihydo-1H-pyrrol-1-yl)ethyl)ureido)ethyl methacrylate It is to be noted that, the substrate is modified by polymerization of e-beam reactive A groups (forming $(A_x)$) and linked to group B to form a modified substrate of formula (I). The modified substrate comprises the group A in polymerized form and not in an e-beam reactive form, the group A is e-beam reactive before the polymerization of A group. The modified substrate is used for different applications, such as an immunoassay.

Without intending to be limited to a particular mechanism of action, as used herein, the term "e-beam reactive moiety," designated as "A" in Formula (I) refers to any chemical functional group that is believed to be self-polymerized when subjected to e-beam irradiation. Exemplary e-beam reactive moieties include but are not limited to those compounds that comprise a methacrylate, an acrylate, an acrylamide, a vinyl ketone, a styrenic, a vinyl ether, a vinyl-containing moiety, an allyl-containing moiety, a benzyl-based compound, and a tertiary-carbon ($CHR_3$)-based compound, or two or more of the e-beam reactive moieties set forth above. Moreover, one of skill in the art could envision other appropriate e-beam reactive moieties for use in the invention based on this representative list.

As noted, in formula (I), a B group facilitates reaction with chemical groups, for example, an amine group presents on a biomolecule of interest and facilitates immobilization of a biomolecule on the porous membrane. In some embodiments, the B group is a reactive group selected from maleimide, iodoacetamide, bromide, N-hydroxysuccinimide-ester (NHS-ester), anhydride or combinations thereof. In some embodiments, the grafted polymer may contain more than one type of B moiety. In these embodiments, the poly$(A)_x$-linkage-B is a copolymer. In the case of the copolymer, B comprises one or more different reactive groups in either a random or well defined pattern.

In one or more embodiments, the B group is an N-hydroxysuccinimide-ester (NHS-ester) compound. The B group may be an N-hydroxysuccinimide-ester (NHS-ester) group-containing compound selected from 2,5-dioxopyrrolidin-1-yl methacrylate or 2,5-dioxopyrrolidin-1-yl acrylate. In a particular embodiment, the B functional group is an NHS-ester group derived from an NHS-ester group-containing compound, for example 2,5-dioxopyrrolidin-1-yl acrylate. In these aspects of the porous membrane (e.g., a nitrocellulose membrane), the membrane may comprise grafted polymers of a compound such as 2,5-dioxopyrrolidin-1-yl acrylate.

The examples of iodoacetamide used to form grafted polymer on the porous substrate may include but are not limited to:

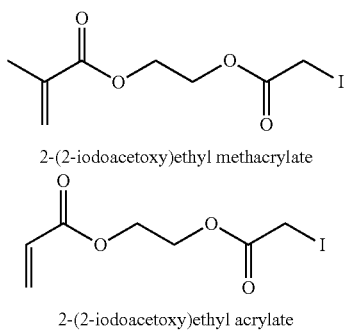

2-(2-iodoacetoxy)ethyl methacrylate 2-(2-iodoacetoxy)ethyl acrylate

The examples of bromide used to form the grafted polymer on the porous substrate may include but are not limited to:

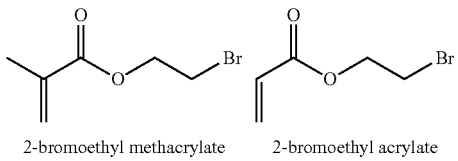

2-bromoethyl methacrylate    2-bromoethyl acrylate

An example of an anhydride which may be used to form the grafted polymer on the porous substrate includes but is not limited to:

furan-2,5-dione
(maleic anhdride)

In one embodiment, the B group further comprises an epoxide group-containing compound in addition to at least one of the maleimide, iodoacetamide, bromide, N-hydroxysuccinimide-ester (NHS-ester), anhydride group containing compounds or combinations thereof. The epoxy group-containing compound may be selected from a glycidal methylacrylate (GMA), glycidal acrylate, vinyl glycidyl ether, allyl glycidyl ether, methallyl glycidyl ether, or any combination thereof. The B functional group as labeled in the schematic presentation of Formula (I) may further include in addition to at least one of the maleimide, iodoacetamide, bromide, N-hydroxysuccinimide-ester (NHS-ester), anhydride group containing compounds or combinations thereof, without intending to be limited in any way, an epoxy group-containing compound, a polyethylene glycol (PEG), an alkyne group, a hydroxyl group, an amine group, a halogen group, a tosyl group, a mesyl group, an azido group, an isocyanate group, a silane group, disilazanes, sulihydryls, carboxylates, isonitriles, phosphoramidites, nitrenes, hydrosilyl, nitrile, alkylphosphonates and any combination of two or more of these functional moieties.

Examples of epoxides which may be used to form the grafted polymer on the porous substrate include but are not limited to:

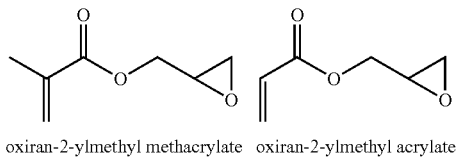

oxiran-2-ylmethyl methacrylate   oxiran-2-ylmethyl acrylate

While not meant to be limited to a particular mechanism of action, the B functional group may be introduced on the porous membrane through e-beam irradiation leading to a self-polymerization of the e-beam reactive moiety, which in turn covalently links (grafts) the B functional group onto the porous membrane while leaving the B functional group available to react with appropriate chemical moieties, for example, an amine, thiol, or other nucleophilic group present on a biomolecule, such as a protein, particularly an antibody, thereby facilitating immobilization of the first biomolecule on the modified porous membrane. This modification is beneficial as many porous membranes, such as unmodified nitrocellulose membranes lack the organic functional groups which are necessary to covalently bind a biomolecule of interest that possesses, for example, an amino group(s) (e.g., proteins, more particularly antibodies) to the porous membrane.

The quantity of the B group present on the modified porous membrane may also have a strong impact on lateral flow test performance. As one skilled in the art would expect, a minimum level of B group must be present to enhance a lateral flow test performance over the corresponding unmodified porous membrane. In case of membranes grafted with 2,5-dioxopyrrolidin-1-yl acrylate (B group =NHS-ester), there is a maximum grafting level and grafting above that maximum level results in reduced lateral flow performance when compared to the corresponding unmodified porous membrane, which is an unexpected observation (FIG. 5). The reduced lateral flow performance above a maximum grafting level for NHS-ester grafted membrane is observed in the presence of high background signal in lateral flow assays. In the case where the modified porous membrane is nitrocellulose grafted with 2,5-dioxopyrrolidin-1-yl acrylate, the HCG lateral flow test performance is improved with less than about 350 μmol of NHS-ester graft per gm of nitrocellulose membrane. Greater than about 450 μmol of NHS-ester graft per gm of nitrocellulose membrane results in reduced HCG test performance enhancement as quantified by test line intensity after subtraction of the background signal (see FIG. 6) compared to unmodified nitrocellulose.

In formula (I), the linkage forms a bond between the poly $(A)_x$ polymer and the B, and the poly $(A)_x$-linkage-B is a polymer coating covalently grafted to the porous membrane. In one or more embodiments, the linkage comprises an ester, an aliphatic chain, a cycloaliphatic chain, an aromatic chain, a heterocyclic compound, a hydrophilic compound, a heteroaromatic compound, or any combination of two or more of the above linkages. In some embodiments, the linkage comprises heteroatoms, such as O, S, N or P. The "linkage" shown in Formula (I) that forms a bond between the poly $(A)_x$ polymer and the functional B group, includes but is not limited to an ester, an aliphatic chain, a cycloaliphatic chain, an aromatic chain, a heterocyclic compound, a hydrophilic compound, a hetero-aromatic compound, or any combination of two or more of these exemplary linkages.

As noted, the method comprises providing a modified porous membrane having the structure of Formula (I) as represented above followed by incubating the modified porous membrane with a first biomolecule, wherein the first biomolecule binds to the modified porous membrane through reaction with the B reactive group to form an activated porous membrane comprising the first biomolecules.

As noted, the first biomolecule binds to the modified porous membrane through reaction with the B reactive group, wherein a bond forms between each of the first biomolecules and the modified porous membrane. In these embodiments, a B reactive group of the polymer grafted membrane reacts with specific chemical groups of the first biomolecule and thereby facilitating immobilization of the first biomolecule on the porous membrane through formation of a covalent bond. For example, when B is an N-hydroxysuccinimide ester group, it reacts with an amine group present on a first biomolecule of interest. In another example, where B is an iodoacetate or maleimide, it reacts with a thiol group present on a first biomolecule of interest to form a covalent bond. In some embodiments, the bond between each of the first biomolecules and the modified porous membrane is a covalent bond. The bonding of a first biomolecule to the modified porous membrane forms the activated porous membrane 16 as shown in FIG. 1.

In some examples, before using the device 30, the activated porous membrane 16 of the device may require a washing of the first biomolecules to remove unbound biomolecules from the activated porous membrane. In these embodiments, the biomolecules which are not specifically bound to the membrane are removed. In some embodiments, the washing step for the first biomolecule bound activated membrane is optional. In these embodiments, the membrane may be used directly after activation of the modified membranes. The washing of the activated porous membrane 16 may be performed using a solution comprising a non-ionic surfactant, and wherein the non-ionic surfactant is polyoxyethylene sorbitan monolaurate.

In some embodiments, once the e-beam induced polymerization is complete, the membrane is washed with water to remove any un-polymerized monomer as well as any polymer that is not grafted to the porous membrane. The removal of un-polymerized monomer as well as any polymer that is not grafted to the porous membrane is advantageous as it eliminates the covalent linkage of the first biomolecules to a B group which is not grafted on the membrane surface. Elimination of linkages between biomolecules and non-grafted B-groups may lead to performance enhancements over un-modified membranes with regard to reducing the quantity of the first biomolecule needed to produce accurate analyte detection. In some embodiments, the membranes are optionally washed with aqueous solutions containing surfactants in order to alter the hydrophilicity of the modified porous membranes and their corresponding fluid flow properties. The control of fluid flow properties may lead to control of the time required for successful analyte detection in a lateral flow assay.

Several of the B groups are water reactive and are known in the art to decompose upon contact with water. The membranes of the present embodiments are capable of retaining the B-group functionality, such as N-hydroxysuccinimide-ester (NHS-ester) functionality on the modified membrane. It is to be noted that washing of the modified porous membranes with water does not lead to loss of reactivity when the B group is NHS-ester. The prevention of loss of activity of the polymer-graft comprising NHS-ester as a B-group after washing of the membrane with water or buffer is an unexpected result as NHS-ester groups generally hydrolyses when exposed to water. Hydrolysis of the modified porous membranes grafted with NHS-ester functionalities results in a porous membrane grafted with polyacrylic acid, as discussed in Example 7. A porous membrane grafted with polyacrylic acid has shown poor performance in lateral flow tests due to the presence of high background signal, as shown in FIGS. 7A and 7B.

In some embodiments, the first biomolecule exhibits improved immobilization on the modified porous membrane relative to immobilization of the first biomolecule on an unmodified porous membrane. The modified porous membranes may allow for increased biomolecule (e.g., DNA, RNA, and protein, particularly an antibody) binding to the porous membrane through formation of a covalent bond between the biomolecule and the porous membrane, thereby leading to improved specificity and sensitivity of immunoassays and diagnostic tests, a reduced number of false positive and false negative test results, or a reduction in the concentration of an analyte requirement for detection.

As noted, in some embodiments of the device 30, the formation of an activated porous membrane 16 may be followed by detection of analytes by adding a biological sample comprising at least an analyte. In these embodiments, the biological sample comprising at least an analyte is added to the sample application zone 10 of the first biomolecule bound activated porous membrane for analyte detection, wherein the analytes are captured by the first biomolecule bound to the modified porous membrane at the test line 14 (FIG. 1). Further, the requirement of concentration of an analyte, such as a biomolecule in a biological sample may be reduced for accurate biomolecule detection in, for example, immunoassays or point-of-care diagnostics by using the activated membranes. This is advantageous particularly for detection of those analytes (such as biomolecules) which are present in biological samples even in small quantities. Activated porous membranes may further shorten the time needed to accurately detect the presence of an analyte, such as a biomolecule, thereby also providing faster positive or negative test results, due to improved immobilization efficiency of the first biomolecules on the activated membranes.

In some embodiments, minimizing non-specific binding of the first biomolecules to a modified porous membrane improves the signal to noise ratio in, for example, immunoassays. In these embodiments, the immunoassays are based on the specific interaction of an antibody (first biomolecule) immobilized on the membrane and an analyte such as a specific biomolecule of interest (e.g., a protein) present in a sample being analyzed to determine the presence or quantity of the analytes such as, biomolecule.

Various porous membranes may be employed for generating the modified porous membrane of the present embodiments. The examples of the unmodified porous membrane may include, but is not limited to, a nitrocellulose membrane, a cellulose membrane, a cellulose acetate membrane, a regenerated cellulose membrane, a nitrocellulose mixed ester membranes, a polyethersulfone membrane, a nylon membrane, a polyolefin membrane, a polyester membrane, a polycarbonate membrane, a polypropylene membrane, a polyvinylidene difluoride membrane, a polyethylene membrane, a polystyrene membrane, a polyurethane membrane, a polyphenylene oxide membrane, a poly(tetrafluoroethylene-co-hexafluoropropylene) membrane, and any combination of two or more of the above membrane.

As noted, in some embodiments, the membrane is a porous membrane, including any commercially available porous membrane, particularly a commercially available nitrocellulose membrane. In certain aspects, a nitrocellulose membrane is chemically modified to comprise, as set forth in Formula (I), a polymer grafted to the membrane surface that facilitates biomolecule (first biomolecule) immobilization on a porous modified membrane. For example, one such modified porous membrane comprises an NHS-ester group-containing compound (e.g, 2,5-dioxopyrrolidin-1-yl acrylate) grafted to a nitrocellulose membrane.

As defined above, nitrocellulose membranes may have any concentration of nitrogen, pore size, or the presence or absence of a backing support. Nitrocellulose membranes have a variety of chemical and physical properties and are routinely used in biological techniques that require, for example, the immobilization of a biomolecule of interest (e.g., an antibody) to a porous membrane or for the collection of biomolecules on these porous membranes in order to separate them from other proteins, nucleic acids, and biomolecules or the like in a biological sample to be analyzed. Any nitrocellulose membrane may be utilized for the modified membrane. Nitrocellulose membranes, which are made of a nitrocellulose polymer, have a strong affinity for high molecular weight DNA, RNA, and protein and prevent the denaturation of such biomolecules.

Figure 2A:
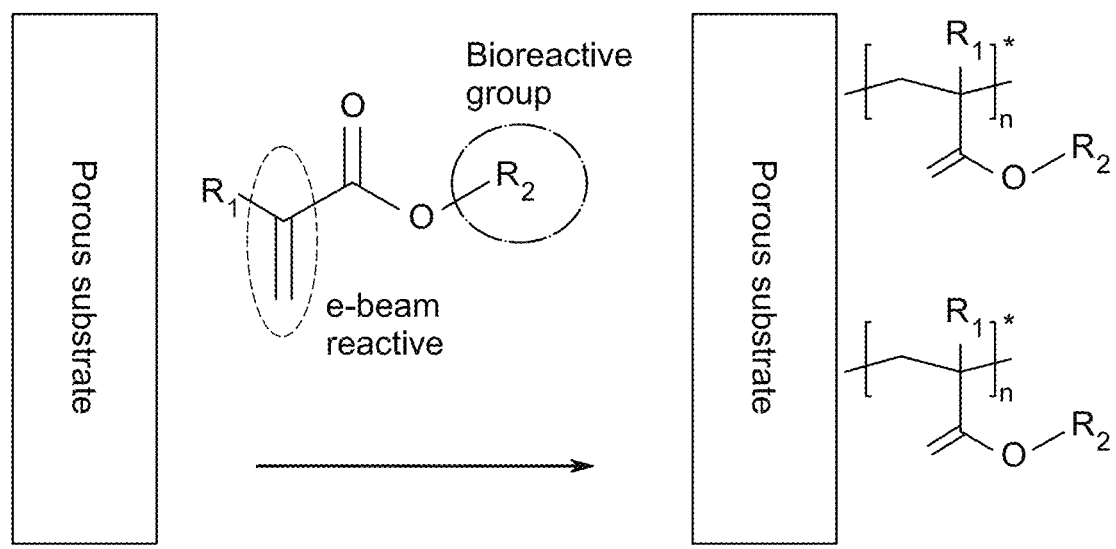

Methods for preparing the porous membranes comprising a polymer coating permanently grafted on the porous membranes are further provided (scheme in FIG. 2A). In some embodiments, a modified porous membrane is grafted with a polymer by first immersing the porous membrane in a solution of a monomer comprising an e-beam reactive moiety (A group), a "linkage" that forms a bond between the poly-$(A)_x$ polymer and a functional B group available to react with a functional moiety present on a biomolecule (see Formula (I)) and then subjected to e-beam to form a polymer, e.g., "poly-$(A)x$ polymer". For example, a porous membrane is immersed in a N-hydroxysuccinimide group-containing compound (e.g., 2,5-dioxopyrrolidin-1-yl acrylate) and then subjected to e-beam irradiation. Alternatively, in other aspects of the invention, the modified porous membranes are prepared by first subjecting a porous membrane to e-beam irradiation followed by immersing the membrane in a solution of, for example, a N-hydroxysuccinimide ester group-containing compound such as 2,5-dioxopyrrolidin-1-yl acrylate, as described above. The methods of production of the modified porous membrane substrates described herein that vary, for example, the ordering of the method steps of immersing and the e-beam irradiation step are encompassed by the method of making the modified membrane.

When used in the context of a method for preparing a modified porous membrane as described in greater detail below, the term "immersing" the porous membrane in a solution of, for example, a N-hydroxysuccinimide ester group-containing compound such as 2,5-dioxopyrrolidin-1-yl acrylate is generally accomplished by dipping the entire porous membrane in the polymeric coating (poly$(A)_x$-linkage-B) solution and then removing any excess solution.

In certain aspects of the invention, the modified porous membranes, particularly nitrocellulose membranes, are prepared as described above using an aqueous solution of monomers to form a polymer graft described herein as (poly$(A)_x$-linkage-B). The solution of monomer may further comprise a co-solvent to improve the solubility of the monomer in water. For example, a surfactant, more particularly a non-ionic surfactant (e.g., polyoxyethylene (20) sorbitan monolaurate (Tween-20™)), may be used as a co-solvent to increase solubility of, for example, 2,5-dioxopyrrolidin-1-yl acrylate, in water. One of skill in the art will appreciate that the appropriate amount of a particular co-solvent (e.g., a nonionic surfactant such as Tween-20™) needed to increase solubility of, for example, an NHS-ester group-containing compound must be determined and optimized experimentally.

Without intending to be limited to a particular method of making a modified porous membrane grafted with a polymer, for example, 2,5-dioxopyrrolidin-1-yl acrylate, exemplary methods of making the modified porous membranes are provided herein. Other methods may also be used to produce the modified porous membranes. In one embodiment, the modified porous membranes are prepared by providing a porous membrane; immersing the porous membrane in a solution of monomers of A group, B reactive group; subjecting the resultant porous membrane to e-beam irradiation to form a polymer of poly$(A)_x$-linkage-B; drying the porous membrane, and thereby preparing a modified porous membrane. Alternatively, the modified porous membranes may be prepared by first subjecting the porous membrane to e-beam irradiation and then immersing the porous membrane in a solution of a monomer A. That is, the modified porous membranes of the invention may be first prepared by providing a porous membrane; subjecting the porous membrane to e-beam radiation; immersing the nitrocellulose membrane in a solution of a monomer to form a polymer on e-beam radiation, drying the porous membrane and thereby preparing a modified porous membrane.

Without intending to be limited to a particular mechanism, in the methods described above for producing a modified porous membrane, particularly a nitrocellulose membrane, e-beam radiation is believed to generate free radicals on the porous membrane which are then available to attack a double bond on, for example, the acrylate group-containing compound, such as, 2,5-dioxopyrrolidin-1-yl acrylate, thereby initiating self-polymerization of the e-beam polymerizable moiety, and resulting in grafting of a polymer on the porous membrane, particularly a nitrocellulose membrane. The functional group B grafted to the porous membrane (e.g., a NHS-ester group) is then available to react with amine and other chemical groups present on a biomolecule of interest, leading to increased binding of the biomolecule to the modified porous membrane compared to the unmodified porous membrane. Increased specific binding of a biomolecule, such as an antibody, can improve the sensitivity and specificity of, for example, immunoassays.

The dosage of e-beam radiation used in the methods of grafting a polymer coating onto a porous membrane is selected to maximize the amount of the polymer coating that is grafted to the porous membrane while also limiting degradation of the porous membrane (e.g., nitrocellulose membrane) known to result from e-beam irradiation. One of skill in the art will recognize that the appropriate dose of e-beam radiation used in the preparation of the modified porous membranes of the invention will need to be optimized experimentally. In particular embodiments, the dose of e-beam radiation used in the methods to prepare a modified porous membrane may be in the range of less than 1 kGy to approximately 50 kGy. The design of assays to optimize parameters such as the amount of the polymer coating, co-solvent, and the dose of e-beam radiation appropriate for use in the methods of the invention is standard and well within the routine capabilities of those of skill in the art.

The modified porous membranes of the invention find use in various biological applications that are dependent upon the immobilization of a biomolecule on a porous membrane (e.g., a nitrocellulose membrane), including but not limited to immunoassays, in vitro diagnostic tests, and techniques for the isolation of a biomolecule of interest. Nitrocellulose membranes are of particular use in biological techniques because of their unique ability to immobilize nucleic acids (e.g., DNA and RNA) for use in Southern and Northern blots and for their binding affinity for amino acids (e.g., protein). As a result of these properties, nitrocellulose membranes are widely used as the substrate in diagnostic tests wherein antigen-antibody binding provides the test result (e.g., home pregnancy tests).

Although the ability of unmodified nitrocellulose membranes to bind biomolecules such as high molecular weight nucleic acids and proteins is beneficial, the modification of porous membranes, particularly nitrocellulose membranes, to facilitate the immobilization of biomolecules (e.g., DNA, RNA, and protein, more particularly an antibody), provides significant advantages over the binding of these biomolecules to unmodified porous membranes (e.g., nitrocellulose membranes).

In one or more embodiments, the first biomolecule is DNA, RNA, or a protein. In some embodiments, the first biomolecule is a protein or peptide. The protein may be a biologically synthesized protein or peptide. In some other embodiments, the peptide may be a synthetically prepared peptide. In one embodiment, the protein biomolecule may include an antibody.

All antibodies are proteins, more specifically glycoproteins, and exhibit binding specificity to an antigen (e.g., a portion of a polypeptide) of interest. In some embodiments of the activated membrane, the term "analyte" is interchangeably used herein as "antigen". In these embodiments, the first biomolecule is an antibody and the captured analyte by the first biomolecule is an antigen. The term "antibody" is used in the broadest sense and covers fully assembled antibodies, antibody fragments that can bind antigen (e.g., Fab', F'(ab)$_2$, Fv, single chain antibodies, diabodies), and recombinant peptides comprising the foregoing. "Antibody fragments" comprise a portion of an intact antibody, preferably the antigen-binding or variable region of the intact antibody. Examples of antibody fragments include Fab, Fab', F(ab')$_2$, and Fv fragments, diabodies, and linear antibodies (Zapata et al. (1995) *Protein Eng.* 8(10):1057 1062), single-chain antibody molecules, and multi-specific antibodies formed from antibody fragments. Any antibody or antibody fragment may be used in the practice of the invention.

In some embodiments, the device 30 may be used for measuring the analyte binding to the activated porous membrane comprising the first biomolecule. The analyte binding to the first biomolecule may also be interchangeably referred to herein as "capture" of the analytes by the first biomolecules attached to the membrane. In these embodiments, the analyte binding to the first biomolecule, such as an antibody, is initiated by adding a biological sample comprising one or more analytes to the first biomolecule bound substrate. In these embodiments, the analyte binding may further be compared with the binding of the analytes to un-modified membranes.

In some embodiments, the detection of antibody binding may be facilitated by coupling the antibody to a detectable substance or a detection probe. Examples of detectable substances include various enzymes, prosthetic groups, fluorescent dye, luminescent materials, bioluminescent materials, radioactive materials, gold particles, polymer beads, particles containing an optical reporter and combinations thereof. Exemplary suitable enzymes include horseradish peroxidase, alkaline phosphatase, (3-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin, a detectable luminescent material that may be couple to an antibody includes but is not limited to luminol; examples of bioluminescent materials include luciferase, luciferin, and aequorin; and examples of suitable radioactive material for detection of antibody binding include $^{125}$I, $^{131}$I, $^{35}$S, or $^3$H.

In some embodiments, the binding of analytes to the first biomolecules may be detected using anti-analytes. The binding of analytes to the first biomolecules may be detected using anti-analytes. In some embodiments, the anti-analytes are biomolecules. The anti-analyte may be added to the analyte bound modified porous membrane, wherein the anti-analytes are specifically bound to the analytes. In some embodiments, the anti-analyte biomolecules comprise DNA, RNA, protein or peptides. In some embodiments, the anti-analyte biomolecule is a protein, such as an antibody. In one embodiment, the anti-analyte biomolecules are an antibody, which may include a monoclonal antibody or a polyclonal antibody.

The device 30 may permit the detection of more than one analyte of the biological sample. In one example embodiment, the analyte is an antigen.

In one or more embodiments, the anti-analyte molecules may be labeled with a detectable substance or detection probe for detection of analytes. The term "detectable substance" and "detection probe" are interchangeably used hereinafter. In some embodiments, the detectable substance comprises an enzyme, a prosthetic group, a fluorescent dye, a luminescent material, a bioluminescent material, a radioactive material, a gold particle, a polymeric bead containing an optical reporter, or combinations thereof. As mentioned, the optical reporter may be defined as a particle containing a dye that absorbs light in the visible region such as quantum dots, gold particles, or carbon black. In one or more embodiments, the detectable substance provides qualitative estimation of analyte binding. In one embodiment, the anti-analyte biomolecules are antibody labeled with a colorimetric substance, such as a gold particle.

An exemplary, albeit not exhaustive list of immunoassays includes a lateral flow assay (e.g., a home pregnancy test), a radioimmunoassay (RIA), an enzyme immunoassay (EIA), an enzyme-linked immunosorbent assay (ELISA), a fluorescent immunoassay, and a chemiluminescent immunoassay. The skilled artisan in the field possesses the skills needed to select and implement the appropriate method(s) for a particular situation, as well as the techniques for performing these immunoassays, as well as the skills to interpret the results. Immunoassays may produce qualitative or quantitative results depending on the particular method of detection selected. The immunoassay may be selected from the group consisting of a lateral flow immunoassay, a radioimmunoassay, an enzyme immunoassay (EIA), an enzyme-linked immunosorbent assay (ELISA), a fluorescent immunoassay, a chemiluminescent immunoassay or combinations thereof.

In one or more embodiments, the biological sample is blood, serum, lymph, urine, saliva, mucus, bodily secretions, cells, tissue or biologically relevant molecules in buffer or saline. Biological samples may be obtained by an individual undergoing the diagnostic test themselves (e.g., blood glucose monitoring) or by a trained medical professional through a variety of techniques including, for example, aspirating blood using a needle or scraping or swabbing a particular area, such as a lesion on a patient's skin Methods for collecting various biological samples are well known in the art.

In certain embodiments, a modified porous membrane comprising a polymer grafted as disclosed herein, is incubated in a solution of a first biomolecule, washing the porous membrane to remove unbound material, and thereby improving immobilization of the first biomolecule to the porous membrane. The porous membrane may be washed in an aqueous solution comprising a surfactant, particularly a non-ionic surfactant, more particularly Tween-20™, to further minimize non-specific binding to the modified porous membrane. In some embodiments, the first biomolecule immobilized on the modified porous membrane, particularly a nitrocellulose membrane, is DNA, RNA, or a protein, such as an antibody.

Methods for improving the sensitivity of an immunoassay are also described herein comprising providing a modified porous membrane comprising the polymer grafting described in detail herein (e.g., a polymer coating of 2,5-dioxopyrrolidin-1-yl acrylate), incubating the modified porous membrane in a solution of a first antibody that specifically binds to an antigen, thereby resulting in immobilization of the antibody on the modified porous membrane forming an activated porous membrane, washing the activated porous membrane to remove excess, non-immobilized antibody, incubating the activated porous membrane comprising the immobilized antibody with a biological sample that may contain the analyte (e.g., antigen) that specifically captures by the immobilized antibody on the activated membrane, and detecting the antigens captured by the antibody immobilized on the activated porous membrane.

Alternatively, the biological sample may be first incubated with a second antibody that specifically binds to the antigen of interest present in the biological sample, wherein the second antibody is conjugated to a detectable substance. The biological sample pre-incubated with an antibody conjugated to a detectable substance is then applied to or incubated with an activated porous membrane comprising a grafted polymer of, for example, 2,5-dioxopyrrolidin-1-yl acrylate with immobilized first antibody. The first antibody captures the antigen bound to the second antibody. The presence of the detectable substance on the antibody permits detection of the antigen in the biological sample being analyzed. Such detectable substances include but are not limited to an enzyme, a prosthetic group, a fluorescent dye, a luminescent material, a bioluminescent material, a radioactive material, a gold particle, a polymeric bead, a particle containing an optical reporter or combinations thereof.

The device as described above, wherein a chemically modified porous membrane (e.g., a nitrocellulose membrane) that possesses improved ability to bind a first biomolecule such as DNA, RNA, or a protein imparts a number of advantages on immunoassays that utilize these modified porous membranes. For example, increased antibody immobilization on the modified porous membrane reduces the amount of antibody needed to detect the presence of an antigen of interest, improved "capture" of the antigen from the biological sample because of the increased amount of antibody immobilized on the modified porous membrane (e.g., a nitrocellulose membrane), leading to an increase in the antigen bound to the immobilized antibody, and a reduced amount of antibody in the biological sample to detect the presence of the biomolecule in the biological sample. Proteins generally have an affinity for unmodified nitrocellulose membrane and are immobilized on the membrane, however, unlike the modified (chemically grafted) nitrocellulose membrane, the immobilized proteins from the un-modified membrane may be removed by washing. For example, when a sample is passed through an unmodified nitrocellulose membrane during a lateral flow assay, the immobilized proteins may be washed off from the membrane. As a result, the first biomolecules may be removed from the un-modified membrane regardless of whether or not it is bound to the analyte of interest, resulting in a decrease in the sensitivity of the analyte binding assay.

As noted, the nitrocellulose membranes are grafted with one or more chemical moieties, such as maleimide, iodoacetamide, NHS-ester or combinations of one or more of these. In some embodiments, the nitrocellulose membranes are grafted with one or more chemical moieties, such as one or more of maleimide, iodoacetamide, or NHS-ester, in combination with an epoxy group.

Figure 2B:
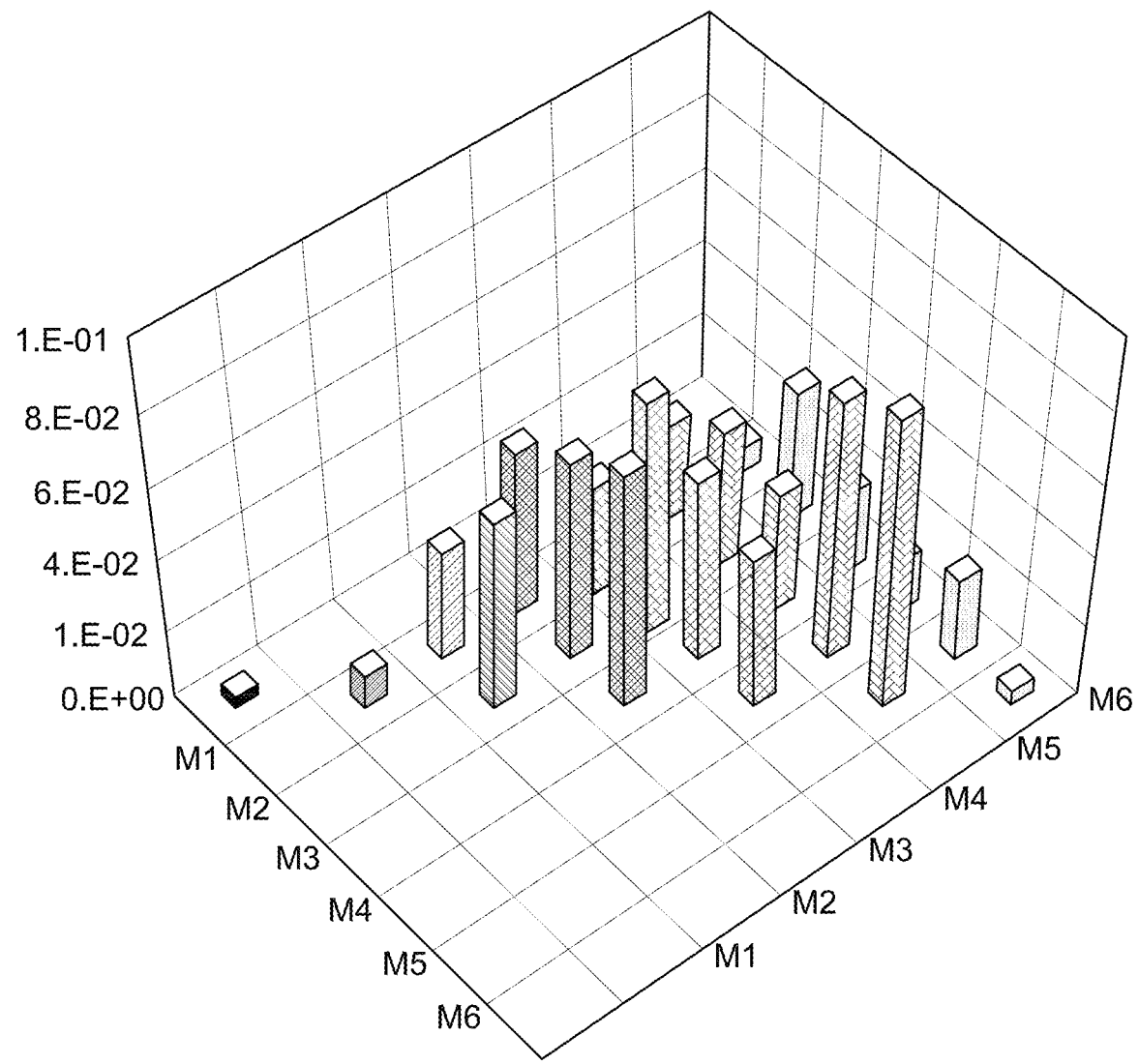

The FTIR data showed (FIG. 2B) grafting efficiency for single or dual groups on nitrocellulose. Further, the percentage weight gain (e.g., relative to that of an unmodified membrane) of the unmodified nitrocellulose membrane ("NC") following NHS-ester or maleimide grafting at various e-beam radiation doses are provided in Table 1. The activated membranes (modified membranes) showed unaltered fluidic properties between modified and unmodified membranes (Table 2) as suggested by comparable capillary rise time in deionized (DI) water.

Figure 3C:
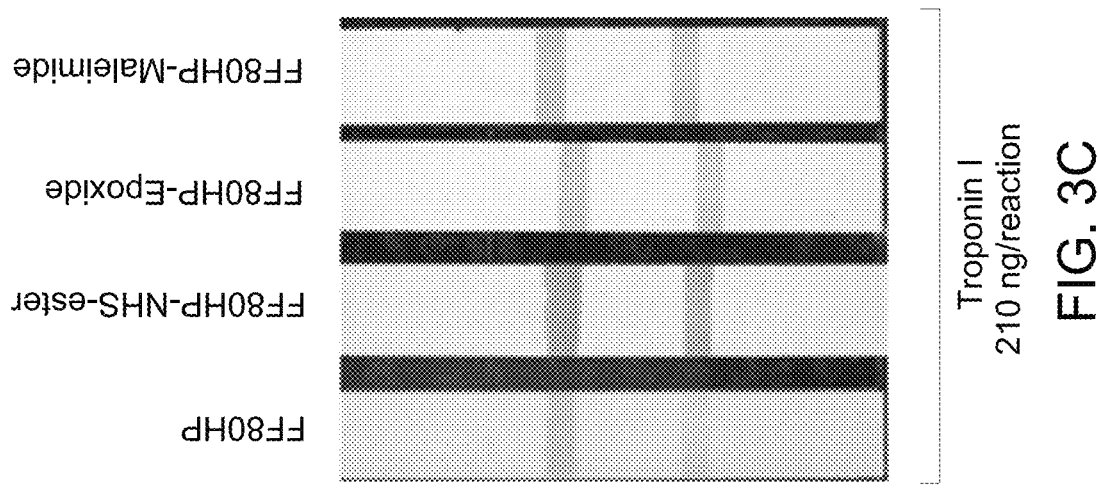
FIG. 3C shows LFA test performance of activated membranes compared to unmodified FF80HP nitrocellulose membranes for the analyte Troponin I.
Figure 3B:
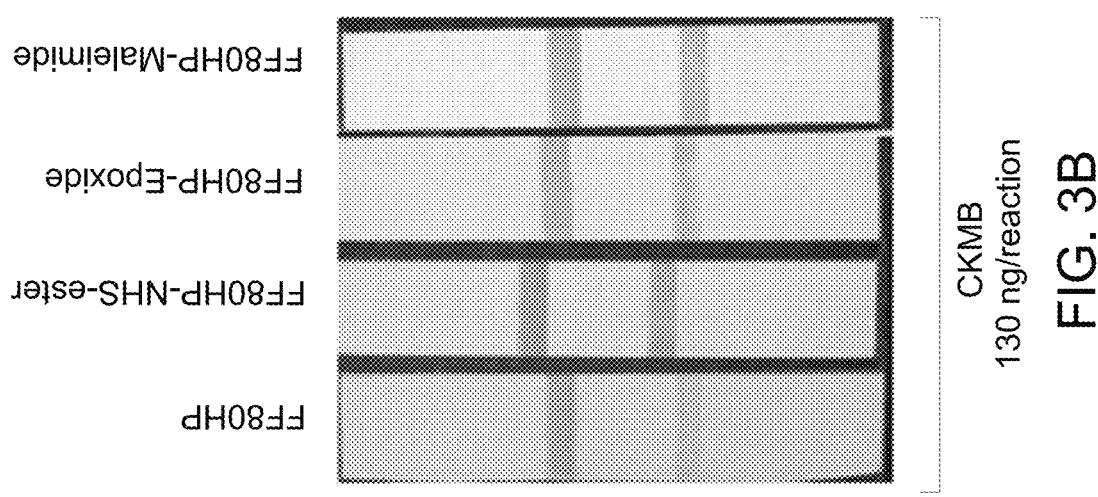
FIG. 3B shows LFA test performance of activated membranes compared to unmodified FF80HP nitrocellulose membranes for the analyte creatine kinase-MB (CK-MB).
Figure 3A:
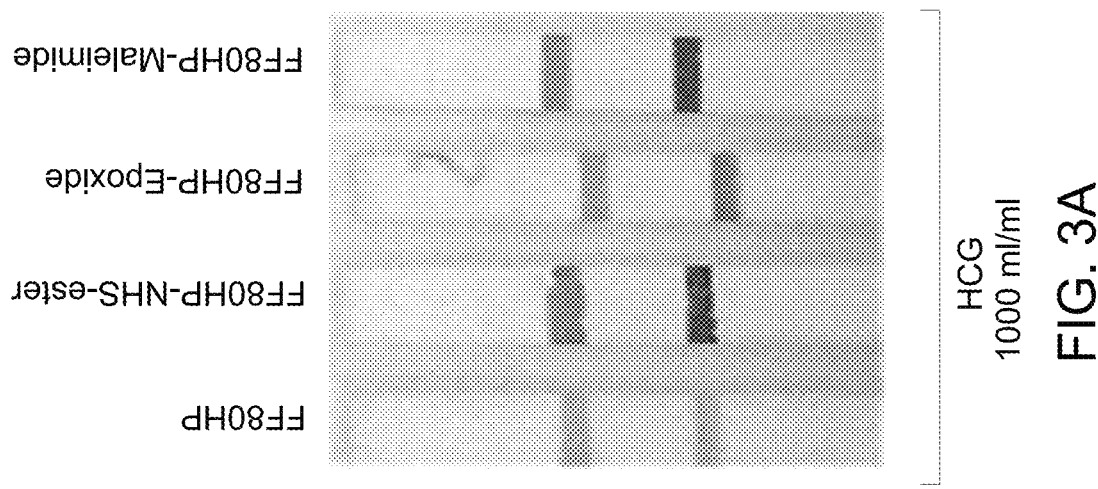
FIG. 3A shows lateral flow assay (LFA) test performance of activated membranes compared to unmodified FF80HP nitrocellulose membranes for the analyte human chorionic gonadotropin (HCG).

The modified nitrocellulose membranes grafted with NHS-ester, maleimide or combination of NHS-ester or maleimide with epoxide may be designed based on the detection of an analyte in lateral flow assay model. The results obtained with the lateral flow assays using unmodified (NC) or modified nitrocellulose membranes grafted with maleimide, epoxide or NHS-ester for HCG (or hCG), CKMB and Troponin I analytes are presented in FIGS. 3A, 3B and 3C, respectively.

The shelf life of different samples, such as analytes captured by the activated membrane was analyzed using HCG as a model biomarker. The test results were analyzed at various times following preparation of the modified porous membranes in order to monitor the stability of modified porous membranes grafted with NHS-ester, maleimide, and epoxide by comparing the grafted membranes to that of the corresponding unmodified porous membrane (FIG. 4A). The same level of improvement in performance was observed, when nitrocellulose membranes grafted with 2,5-dioxopyrrolidin-1-yl acrylate and aged for three months, the nitrocellulose membranes grafted with oxiran-2-ylmethyl 2-methylprop-2-enoate and aged for six months, and the nitrocellulose membranes grafted with 2-(2,5-dioxo-2,5-dihydro-1H-pyrrol-1-yl)ethyl acrylate aged for two months (FIGS. 4B, 4C and 4D respectively) were used. The tests were performed with various HCG concentrations, and the signal intensity improvement of each activated nitrocellulose is summarized in Table 7. Generally, the lower the analyte concentration, the better the improvement in signal intensity, which highlights the increased sensitivity of immunoassays when using the modified porous membranes described herein. A maximum of 5 to 10 fold improvement in sensitivity was observed for nitrocellulose membranes grafted with oxiran-2-ylmethyl 2-methylprop-2-enoate and 2,5-dioxopyrrolidin-1-yl acrylate respectively.

The following examples are offered by way of illustration and not by way of limitation:

EXAMPLES

Example 1

Grafting of Various Functionalities onto a Nitrocellulose Membrane

The preparation of modified porous nitrocellulose membranes (as shown in FIG. 2A) includes: 1) preparation of coating solution that contains methacrylate/acrylate monomers, 2) dip coating of nitrocellulose in the coating solution, 3) exposing the coated membrane to electron beam irradiation (e.g., 10 kGy) to initiate polymerization resulting in grafting of a polymer onto the nitrocellulose membrane, 4) washing the membrane in water to remove co-solvent and un-grafted species, 5) reconditioning the membrane with low concentration of surfactant for better fluidic properties, and 6) drying.

Preparation of coating solution—Tween 20 was used in the formulation in order to both increase solubility of monomers in water and improve grafting efficiency of the membranes. Below are examples for preparation of 100 mL of coating solution for each membrane formulation:

For preparing an NHS-ester grafted nitrocellulose membrane (NC-NHS-ester), a 100 mL of 1:1 Tween 20/water solution was prepared, followed by dissolution of 4 grams of 2,5-dioxopyrrolidin-1-yl acrylate. For preparing a maleimide grafted nitrocellulose (NC-Mal) membrane, a 100 mL of 1:1 Tween 20/water solution is prepared, followed by dissolution of 2 grams of 2-(2,5-dioxo-2,5-dihydro-1H-pyrrol-1-yl)ethyl acrylate. For preparing an epoxide grafted nitrocellulose membrane, oxiran-2-ylmethyl 2-methylpro-2-enoate, Tween 20 and water were mixed at volume ratio of 3:12:85.

Dip coating—The nitrocellulose membrane was dipped into the coating solution to fully saturate the pores, followed by an optional step of removing the residual liquid on top of the membrane with a rubber blade if 50% Tween 20 was present in the dope.

Electron Beam Irradiation—A bench-scale electron beam irradiation unit was used (AEB, Advanced Electron Beam, e-Beam unit, EBLAB-150), with operation voltage of 125 kV, and electron dosage delivery of 10 kGy which was sufficient to graft moieties to nitrocellulose membranes while minimizing free radical degradation of nitrocellulose.

Washing—The grafted nitrocellulose membrane was washed three (3) times with deionized water for 30 minutes each at room temperature in order to remove the Tween 20 and non-grafted species.

Reconditioning—In order to achieve good surface properties and capillary rise behavior, the modified membrane was treated with an aqueous surfactant solution at room temperature.

Drying the grafted membrane—The nitrocellulose membrane was dried overnight at 50° C. and 25 mm Hg, and chemical physical characterizations were performed thereafter. Alternatively, the modified porous nitrocellulose membranes were dried overnight at ambient temperature and atmospheric pressure.

In certain experiments, the nitrocellulose membranes were first exposed to e-beam radiation and then dipped in the aqueous coating solution.

The percentage weight gain of the unmodified FF80HP nitrocellulose membrane ("NC") (from GE Healthcare) grafted with NHS-ester, maleimide, or epoxide groups relative to that of an unmodified membrane is provided in Table 1. The weight gain is expressed as the percentage weight gain relative to that of unmodified nitrocellulose membrane, as appropriate.

The increase in weight following the grafting process set forth above supports the successful introduction of maleimide, NHS-ester, or epoxide on the nitrocellulose membranes.

To further confirm the successful grafting on the porous membranes, nitrocellulose membranes were analyzed by ATR FT-IR using a PerkinElmer Spectrum 100 FTIR spectrophotometer (PerkinElmer Life and Analytical Sciences, Sheraton, Conn.). In ATR-FTIR (as shown in FIG. 2) the generation of a new carboxylic group on nitrocellulose as a result of modifications is indicated by a carbonyl stretch at around 1730 $cm^{-1}$ on the spectrum. The ratio of the peak height to one of the nitrocellulose nitro peaks at 1640 $cm^{-1}$ was calculated for the purpose of analyzing chemistry grafting uniformity of grafting.

Example 2

Properties of Modified Nitrocellulose Membranes Grafted with NHS-Ester, Maleimide or Epoxide or Combinations Thereof The modified nitrocellulose membranes grafted with 2,5-dioxopyrrolidin-1-yl acrylate, 2-(2,5-dioxo-2,5-dihydro-1H-pyrrol-1-yl)ethyl acrylate, or oxiran-2-ylmethyl 2-methylpro-2-enoateas described above were further characterized to assess membrane thickness, capillary rise, and mechanical strength (e.g., stress and strain). The modified nitrocellulose membranes were grafted as described in Example 1.

Capillary rise was tested using an Ontario Die 10 mm with a 50 mm notched punch to cut test strips from unmodified and modified nitrocellulose membranes grafted with 2,5-dioxopyrrolidin-1-yl acrylate, 2-(2,5-dioxo-2,5-dihydro-1H-pyrrol-1-yl)ethyl acrylate, or oxiran-2-ylmethyl 2-methylpro-2-enoate. The test strips were placed in a device to keep the test membrane strips vertical. The device also has a shallow groove to hold the test fluid (e.g., distilled water). The rise time of 100 μL of distilled water to the notch at a height of 40 mm was recorded. The capillary rise of replicate samples of unmodified and modified nitrocellulose membranes was measured. An assay time in HCG half stick test was also measured. In a HCG half stick test, a total of 100 μl running buffer containing target analyte was applied to the stick and flew through the half stick device, which comprise both a nitrocellulose membrane and an absorbent pad. The results are summarized below in Table 2.

TABLE 1

Weight gain of nitrocellulose membranes following grafting with different coating materials

| | Concentration in coating formulation, wt % | | | |
|---|---|---|---|---|
| Activated Membranes | Maleimide-acrylate | Epoxide-methacrylate | NHS-acrylate | Weight gain (%) |
| FF80HP | | | | |
| 1 | 2 | | | 1.8 |
| 2 | | 3 | | 15.8 |
| 3 | | 6 | | 23.7 |
| 4 | 2 | 6 | | 27.7 |
| 5 | | | 4 | 5.3 |
| 6 | | 6 | 4 | 19.3 |
| 7 | | 3 | 2 | 6.5 |
| 8 | | 6 | 1 | 22.0 |

TABLE 2

Characterization of modified FF80HP nitrocellulose membranes grafted with maleimide, epoxide, and/or NHS-ester.

| | Concentration in coating formulation, wt % | | | Capillary rise (s) | | Assay time in half stick HCG test (min) |
|---|---|---|---|---|---|---|
| Activated Membranes | Maleimide-acrylate | Epoxide-methacrylate | NHS-acrylate | Ave. | STDEV | |
| FF80HP | | | | 81 | | 40 |
| 1 | 2 | | | 96 | 7.8 | 28 |
| 2 | | 3 | | 146 | 1.7 | 33 |
| 3 | | 6 | | 121 | 1.7 | 24 |
| 4 | 2 | 6 | | 100 | 3.5 | 28 |
| 5 | | | 4 | 121 | 4.0 | 28 |
| 6 | | 6 | 4 | 100 | 4.0 | 33 |
| 7 | | 3 | 2 | 135 | 5.5 | 29 |
| 8 | | 6 | 1 | 112 | 9.2 | 30 |

Example 3

High-Throughput Screening of Modified Membranes

To quickly screen membrane modifications across a suite of capture antibody candidates, high throughput screening experiments were performed. Modifications and performance testing were performed in a 96-well vacuum manifold (S&S Manifold I). Each well represents a different combination of modification, which further comprises antibody. For modification purpose, unbacked nitrocellulose (AE98, GE healthcare) were clamped in place between both top and bottom layers of the manifold, followed by adding various aqueous solutions containing e-beam reactive monomers comprising functionalities of maleimide (M1), iodoacetatamide (M2), epoxide (M3), bromide (M4), NHS-ester (M5), maleic anhydride (M6) or a combination of any two functionalities mentioned above. Different functional moieties used for membrane modifications are shown in Table 3. The membrane was then e-beam treated in the 96-well manifold, followed by washing extensively in water to remove unreacted species and co-solvent.

TABLE 3

Different functional moieties used for membrane modification and different examples

| Compound ID | Chemical Structure & Name | Functionality |
|---|---|---|
| M1 | 2-(2,5-dioxo-2,5-dihydro-1H-pyrrol-1-yl)ethyl acrylate | Maleimide |
| M2 | 2-(2-iodoacetoxy)ethyl methacrylate | Iodoacetamide |
| M3 | oxiran-2-ylmethyl methacrylate | Epoxide |
| M4 | 2-bromoethyl acrylate | Bromide |
| M5 | 2,5-dioxopyrrolidin-1-yl acrylate | NHS-ester |
| M6 | furan-2,5-dione (maleic anhdride) | Maleic anhydride |

To test the functionality of each modification strategy in binding various antibodies, the modified membranes were placed in a chamber over a layer of Bio-Rad #170-3955 blotting paper and clamped back in the 96-well manifold such that the wells were aligned with the treated areas of the membrane. HCG, troponin I or CK-MB antibodies (see table 5 for sources of these antibodies) were prepared at concentrations of 2.8 µg/µL. The same inkjet dispensing formulation ("ink") as used for lateral flow assay test strips (30% glycerol, 0.1% triton X-100, 0.3% carboxyl methylcellulose (CMC)) was employed. 2 µL of ink solutions were added to each well, such as adding an assay mixture with antibody for test wells, and an assay mixture without antibody for control wells. Membranes were dried at room temperature for 48-72 hours to allow capturing the antibodies in adequate time to enhance binding. To reduce non-specific binding, each well was subsequently treated with 200 µL of lateral flow assay (LFA) buffer containing 1% BSA for 2 hours which was then removed using vacuum.

The effect of membrane treatment on assay performance was determined by mixing HCG, troponin I and CK-MB target proteins with an excess of the appropriate fluorescently labeled detection antibodies (prepared using a GE Amersham fluorolink CY5 labeling kit according to the manufacturer's instructions). The antibody-target mixtures (100 µL) were added to the wells and placed on an orbital shaker for 15 minutes. The unbound label and target molecules were then removed by washing with PBST buffer under vacuum. The membrane was then removed from the vacuum apparatus, washed for 2 hrs in PBST buffer and protected from light on an orbital shaker and then imaged on a GE Typhoon 9400 fluorescence scanner Image J software (Free software from NIH) was then used to analyze the signal intensity from each well so that the signal ratios from treated and untreated membrane was possible to calculate. The data showing improvement in binding individual antibody for each modification strategy is summarized in Table 4. In summary, among a suite of functionalities, NHS-ester, epoxide, and maleimide were showing superior binding performance across antibodies when they were present on the nitrocellulose membrane surfaces. For this reason, the above chemicals were selected for membrane grafting for lateral flow immunoassay performance evaluations.

TABLE 4

96-well plate membrane modification and antibody binding testing performance

| Membrane modifications by functional moieties | Normalized antibody binding performance of modified membranes against unmodified | | |
|---|---|---|---|
| | HCG | Troponin I | CKMB |
| Untreated | 1 | 1 | 1 |
| M1 | 2.8 | 5.1 | 4.6 |
| M2 | 1.8 | 1.6 | 2.4 |
| M3 | 6.3 | 3.1 | 2.7 |
| M4 | 3.8 | 2.2 | 1.9 |
| M5 | 0.5 | 6.2 | 0.2 |
| M6 | 2.1 | 2.4 | 0.8 |
| M1, M2 | 1.8 | 3.2 | 3.1 |
| M1, M3 | 1.1 | 2.7 | 2.7 |
| M1, M4 | 3.7 | 2.1 | 2.3 |
| M1, M5 | 2.3 | 4.8 | 0.5 |
| M1, M6 | 3.5 | 4 | 3.1 |
| M2, M3 | 2.7 | 2 | 3.3 |
| M2, M4 | 1.9 | 1.4 | 2.3 |
| M2, M5 | 1.6 | 2.7 | 2.6 |
| M2, M6 | 1.2 | 1.9 | 1.4 |
| M3, M4 | 1.6 | 1.3 | 1.2 |
| M3, M5 | 3 | 3.6 | 1.3 |
| M3, M6 | 4.2 | 2.6 | 1.7 |
| M4, M5 | 2 | 4.9 | 1.2 |
| M4, M6 | 1.9 | 3.4 | 1.9 |
| M5, M6 | −0.3 | 4.2 | 0.1 |

Example 4

Use of Modified Nitrocellulose Membranes in Lateral Flow Assays

Lateral flow assays that require the immobilization of a protein, more particularly an antibody, on a solid phase material form the basis of a number of in vitro diagnostic tests. One common example of this technology is commercially available home pregnancy tests which rely on the immobilization of an antibody that recognizes human chorionic gonadotropin (HCG), a hormone that is produced in high levels during pregnancy. Techniques to assess the utility of the modified FF80HP nitrocellulose membranes grafted with 2,5-dioxopyrrolidin-1-yl acrylate, 2-(2,5-dioxo-2,5-dihydro-1H-pyrrol-1-yl)ethyl acrylate, or oxiran-2-ylmethyl 2-methylpro-2-enoate in lateral flow assays were designed based on the pregnancy test model. The tests were normalized against baseline performance of FF80HP as control sample.

A control and a test line were created on unmodified or modified FF80HP nitrocellulose membranes grafted with NHS-ester, maleimide or epoxide by inkjet printing on a Dimatix DMP-2800 Piezoelectric Inkjet printer in accordance with standard techniques in the art. A basic inkjet formulation containing glycerol, Triton X-100, and CMC was used to prepare the control line further contained 1.2 mg/mL goat anti-mouse IgG. The test line ink contains 1 mg/mL primary antibody against HCG, CK-MB, or Troponin I (see Table 5 for antibody list).

Gold particles conjugated with anti-HCG-beta (purchased from Abcam) were used for HCG lateral flow tests. The gold nanoparticle conjugate with anti-troponin I or anti-CKMB was prepared from a solution of 40 nm gold particles (DCN #CG020). 1.0 mL of the gold particle solution was added to three different 1.5 mL eppendorf tubes and 3 µL of 0.2 M $K_2CO_3$ was added to each tube, mixed and allowed to stand for 10 minutes. 14 µg/mL of the Troponin I or CKMB antibody of choice was added to each tube and mixed for 10 minutes after which 100 µL of 10% BSA in PBS was added and mixed for 10 minutes. The gold particles were pelleted by centrifugation at 5,000×g for 20 minutes. After discarding the supernatant the pellets were re-suspended in 15 µL of 0.1% BSA. The re-suspended pellets were pooled and the tubes were washed with 160 µL of conjugate solution (Conjugate Solution: 3% Trehalose+0.5% BSA+1.0% Tween 20 in 10 mM PBS).

TABLE 5

Antibodies used for immunoassays

| Antibodies for lateral flow sandwich assay | Primary antibody (printed on test line) | Secondary antibody (conjugated with gold) |
|---|---|---|
| HCG | Anti-HCG-alpha, Abcam, ab20750 | Anti-HCG-beta, Abcam, ab31206 |
| CK-MB | Anti-CKMB, Fitzgerald 70-xg47 | Anti-CKMB, Fitzgerald 10R-3127 |
| Troponin I | Anti-Troponin I, Fitzgerald 70-B9085GA01-A0 or 10-T79C | Anti-Troponin I, Fitzgerald 10R-T123g |

Nitrocellulose printed with antibodies was laminated onto G&L polyester backing pre-treated with GL 187 glue, followed by lamination of a 27 mm Whatman CF7 absorbent pad on the top. The half-stick pads were then cut into 5 mm length running strips using a guillotine cutter. Analyses were conducted by placing the half-stick strips into 100 µL of LFA running buffer containing various HCG (Sigma Aldrich), troponin I (Fitzgerald cat. #30-AT63) or CKMB (Fitzgerald cat #30-AC67) concentrations, 0.5% Tween 20 as the blocking molecule, and gold-antibody conjugate targeted against HCG, CK-MB or Troponin I (see Table 5 for antibody list). After 30 minutes the assay was completed, the test strips were photographed and the line intensities analyzed using Image J. The colorimetric reporting signal intensity was assessed both by ImageJ analysis to obtain a quantitative comparison. In quantitation process, an image of the lateral flow strips was obtained via an optical scanner, and the image J was then used to separate out the green channel from the image, followed by intensity mapping across the entire strip on a grey scale. The signal intensity at the test line was normalized by subtracting the background signal from the test line on each strip. The results obtained with the lateral flow assays are presented in FIGS. 3A, 3B and 3C for HCG (1000 mIU/ml), CKMB (130 ng/reaction) and Troponin I (210 ng/reaction) using unmodified FF80HP NC or modified nitrocellulose membranes grafted with 2-(2,5-dioxo-2,5-dihydro-1H-pyrrol-1-yl)ethyl acrylate or NC-Maleimide, oxiran-2-ylmethyl 2-methylpro-2-enoate or NC-epoxide, or 2,5-dioxopyrrolidin-1-yl acrylate or NC-NHS-ester.

The colorimetric reporting signal was visible within approximately 3-5 minutes in the assays performed with the unmodified nitrocellulose membranes and within about only 1 minute in those assays that used the modified nitrocellulose membranes. No difference in the background signal was observed between the unmodified and modified nitrocellulose membranes during the time frame of the assay.

The performance of the activated FF80HP nitrocellulose membranes was demonstrated across different analytes and analyte concentrations. A clear improvement in performance for all three activated membranes is demonstrated for all three analytes tested, for example in pregnancy test under 1000 mIU/ml HCG concentration (FIG. 3A), CK-MB test under 130 ng per reaction (FIG. 3B), and Troponin I test under 220 ng/rxn (FIG. 3C), with significant improvement observed for both NC-NHS-ester and NC-Maleimide-grafted membranes compared to NC-epoxide. The ability of various activated membranes in improving signal intensity of lateral flows as a function of both analyte and analyte concentration is summarized in Table 6, which clearly shows improvement of test performance in both sensitivity and detection limit by activated nitrocellulose membranes over non modified nitrocellulose.

respectively. The same level of improvement in performance was observed, such as when NC-NHS-ester was aged for 3 months (FIGS. 4B and 4F), NC-epoxide was aged for 3 months (FIGS. 4C and 4G), and NC-Maleimide was aged for 1.5 months (FIGS. 4D and 4H). For FIG. 4A, FIG. 4B, FIG. 4C, and FIG. 4D the days of aging are shown (also mentioned in Table 7 below) for unmodified FF80HP NC, NC-NHS-ester, NC-epoxide and NC-maleimide, respectively. The tests were performed under various HCG concentrations, and signal intensity improvement of each activated nitrocellulose was summarized in Table 7.

TABLE 7

Performance improvement of aged activated FF80HP membranes in HCG test

| | HCG, | FF80HP | | | | FF80HP-NHS-ester | | | |
|---|---|---|---|---|---|---|---|---|---|
| | mIU/ml | Day 243 | Day 252 | Day 315 | Day 360 | Day 1 | Day 10 | Day 50 | Day 96 |
| Signal intensity | 50.00 | 1.01 | 0.75 | | 0.80 | 12.83 | 11.77 | | 9.72 |
| | 100.00 | 4.74 | 3.64 | | 3.91 | 24.46 | 22.18 | | 26.17 |
| | 1000.00 | 25.15 | 25.90 | 22.26 | 22.26 | 75.35 | 77.97 | 72.25 | 69.34 |
| Signal ratio to untreated FF80HP | 50.00 | | | | | 12.65 | 15.77 | | 12.08 |
| | 100.00 | | | | | 5.16 | 6.10 | | 6.70 |
| | 1000.00 | | | | | 3.00 | 3.01 | 3.25 | 3.11 |

| | HCG, | FF80HP-epoxide | | | | FF80HP-Maleimide | | | |
|---|---|---|---|---|---|---|---|---|---|
| | mIU/ml | Day 1 | Day 10 | Day 60 | Day 105 | Day 1 | Day 10 | Day 42 | Day 88 |
| Signal intensity | 50.00 | 4.88 | 4.71 | | 3.75 | 11.18 | 11.41 | | 2.32 |
| | 100.00 | 9.08 | 8.51 | | 9.16 | 22.63 | 22.53 | | 6.12 |
| | 1000.00 | 49.16 | 47.69 | 42.28 | 42.28 | 78.49 | 75.48 | 71.17 | 27.95 |
| Signal ratio to untreated FF80HP | 50.00 | 4.81 | 6.31 | | 4.67 | 11.02 | 15.29 | | 2.89 |
| | 100.00 | 1.91 | 2.34 | | 2.35 | 4.77 | 6.19 | | 1.57 |
| | 1000.00 | 1.95 | 1.84 | 1.90 | 1.90 | 3.12 | 2.91 | 3.20 | 1.26 |

TABLE 6

Performance improvement of activated membranes in LFA across analytes against unmodified nitrocellulose (FF80HP).

| Marker Antibody | | FF80HP--Maleimide | FF80HP--Epoxide | FF80HP-NHS-ester |
|---|---|---|---|---|
| HCG | 1000 | 3.0 | 2.2 | 3.0 |
| mIU/ml | 100 | 5.2 | 2.5 | 5.6 |
| | 50 | 13.6 | 6.0 | 15.9 |
| Troponin I | 210 | 4.2 | 2.6 | 2.8 |
| ng/rxn | 6 | 4.1 | 3.3 | 4.4 |
| CK-MB | 130 | 2.7 | 2.2 | 3.0 |
| ng/rxn | 7 | 1.9 | 1.1 | 2.2 |

Example 5

Determination of Shelf Life of the Modified Grafted Membranes

NC-epoxide, NC-NHS-ester, and NC-Maleimide were stored under room temperature with 50% relative humidity. The performance of the aged samples in HCG test was analyzed at various times in order to monitor shelf life of these samples using NC-NHS-ester, NC-epoxide, and NC-Maleimide (FIGS. 4B, 4C and 4D respectively) compared to control (FIG. 4A). The signal intensity of the bands in FIGS. 4A, 4B, 4C and 4D were measured using Image J analysis and illustrated in graphs of FIGS. 4E, 4F 4G and 4H, Example 6

HCG Test Performance as a Function of NHS Ester Level on the Membrane

NC-NHS ester membranes were prepared with different level of NHS-ester grafting on the NC membrane by adjusting monomer concentration in the grafting dope formulation. The HCG test performance was analyzed at various concentrations of NHS ester grafting on the NC membrane in order to determine the concentration of NHS-ester graft, which provides maximum efficiency for lateral flow. HCG test performance was determined at 1000 mIU/ml HCG using the 100 µl of running buffer PBS containing 0.5% tween 20 and 0.15 mg/ml Gold-anti-HCG-β.

The results of the HCG test performance is shown in FIG. 5, wherein nitrocellulose membranes grafted with a low (50 µmol of NHS-ester graft per gm of nitrocellulose membrane), optimal (300 µmol of NHS-ester graft per gm of nitrocellulose membrane) and a high (450 µmol of NHS-ester graft per gm of nitrocellulose membrane) concentration of 2,5-dioxopyrrolidin-1-yl acrylate (mentioned in FIG. 5, FF80HP-NHS-ester) are compared to unmodified nitrocellulose (FF80HP). The improvement in performance was observed at the optimal concentration of grafted 2,5-dioxopyrrolidin-1-yl acrylate (FIG. 5). The high concentration of grafted 2,5-dioxopyrrolidin-1-yl acrylate on nitrocellulose causes non-specific binding, resulting in a high background signal and low signal to noise.

The reduced lateral flow performance above a maximum grafting level for NHS-ester grafted membrane was observed (FIG. 5) in the presence of high background signal in lateral flow assays. The HCG lateral flow test performance was improved for the nitrocellulose grafted with 2,5-dioxopyrrolidin-1-yl acrylate, with less than about 350 µmol of NHS-ester graft per gm of nitrocellulose membrane. Greater than about 450 µmol of NHS-ester graft per gm of nitrocellulose membrane resulted in reduced HCG test performance enhancement as quantified by test line intensity after subtraction of the background signal (see FIG. 6) compared to unmodified FF80HP nitrocellulose.

The FIG. 6 shows a ratio of the background corrected test line intensity for nitrocellulose grafted with NHS-ester and the corresponding unmodified membrane as a function of the quantity of NHS-ester grafted on the membrane at three different concentrations of HCG. In addition to loss of improvement at NHS-ester concentrations at greater than about 450 µmol/g of nitrocellulose, the performance improvement was greater compared to unmodified nitrocellulose when lower concentrations of analytes (HCG) were used. This supports the facts that the modified membrane improves the sensitivity.

The quantity of NHS-ester functionality grafted onto nitrocellulose membranes was measured as follows. $H_2O$ (1 mL/10 mg of modified nitrocellulose membrane with the backing) was added to a massed piece of nitrocellulose membrane grafted with 2,5-dioxopyrrolidin-1-yl acrylate in a glass 2 dram vial. The vial was then swirled on an orbital shaker at 100 rpm for 40 min. Once swirling was complete, the $H_2O$ was removed and an equal volume of 0.1 M $NH_4OH$ was added to the membrane in the glass vial. The vial was again swirled on an orbital shaker at 100 rpm for 40 min. Once swirling was complete, the absorbance of the ammonium 2,5-dioxopyrrolidin-1-olate resulting from hydrolysis of the membrane grafted NHS-ester was measured at 260 nm and converted to concentration using a molar absorptivity of 9297 $M^{-1}cm^{-1}$. The concentration was converted to µmol NHS-ester/g NC using the assumption that 80% of the modified porous membrane with the backing mass was from the backing and the remaining 20% was from the modified nitrocellulose membrane.

Example 7

Acrylic Acid Grafted Nitrocellulose (NC-AA) Membrane for Lateral Flow Assay

The degradation of NHS-ester, such as 2,5-dioxopyrrolidin-1-yl acrylate grafted on NC results in acrylic acid graft on the nitrocellulose (NC-AA) bearing —COO⁻ group. Acrylic Acid grafted FF80HP nitrocellulose or NC-AA membrane was prepared by dipping FF80HP NC in acrylic acid aqueous solution, followed by e-beaming, washing and drying. Lateral flow assay test performance was determined by striping NC or NC-AA with goat-anti-mouse IgG, followed by running in 100 µl PBS buffer containing 0.5% tween 20 and 0.15 mg/ml and Gold-mouse-anti-HCG-β. FIGS. 7A and 7B show the lateral flow assay strips determined after 2 mins (t=2 mins) and 20 mins (t=20 mins) respectively after starting the lateral flow (t=0). The negative charges on NC-AA prevented Gold-anti-HCG-β from flowing through smoothly, causing aggregation of gold particles on the membrane (as shown in FIG. 7B). While on the unmodified FF80HP NC, Gold-anti-HCG-β was able to flow through and been captured by the stripped goat-anti-mouse IgG line. The electrostatic interaction between charged surface and antibody prevents gold conjugate from flowing properly through the membrane, which is shown in FIGS. 7A and 7B.

Example 8

Performance of the Modified Membrane Over Commercially Available Products

Performance of the modified membrane over commercially available products was assessed using the modified FF80HP nitrocellulose membranes grafted with 2,5-dioxopyrrolidin-1-yl acrylate, 2-(2,5-dioxo-2,5-dihydro-1H-pyrrol-1-yl)ethyl acrylate and the membrane grafted with oxiran-2-ylmethyl 2-methylpro-2-enoate in lateral flow assays, which were designed based on the pregnancy test model. The tests were normalized against baseline performance of FF80HP as control sample. A control (C) and a test line (T) were created on unmodified, modified nitrocellulose membranes and commercially available membranes by inkjet printing on a Dimatix DMP-2800 Piezoelectric Inkjet printer in accordance with standard techniques in the art. A basic inkjet formulation containing glycerol, Triton X-100, and CMC was used to prepare the control line further contained 1.2 mg/mL goat anti-mouse IgG. The test line ink contains 1 mg/mL primary antibody against HCG. The method is same as described in Example 4 above. HCG test performance in half stick using lateral flow assay was determined by striping various membranes with same density of test or control line antibodies. The strips of membranes were used for running 100 µl PBS buffer containing 0.5% tween 20, 0.15 mg/ml gold-labelled-anti-mouse HCG-β, and 1000 mIU/ml HCG.

The performance of modified nitrocellulose membranes was then compared to a broader range of commercially available products as shown in FIGS. 8A and 8B. For example, the performance of the modified nitrocellulose membranes was compared with commercially available membranes with comparable fluidic properties designated as CP (commercially available product), and two different grades of membranes from GE Healthcare designated as FF120HP and FF80HP in FIG. 8A. The signal intensity of the bands were measured using Image J analysis and illustrated in FIG. 8B. As shown in FIGS. 8A and 8B, both nitrocellulose membranes functionalized with either epoxide or NHS-ester groups were able to improve HCG test signal intensity at 1000 mIU/ml HCG compared to unmodified nitrocellulose membranes. The data (FIGS. 8A and 8B) supports the fact that the membrane modification by polymer grafting increases the immobilizing efficiency of antibodies on membranes, which further enhance the lateral flow immunoassay performances.

The invention claimed is:
1. A lateral flow immunoassay device comprising:
a sample application zone at one end of the lateral flow immunoassay device for applying a biological sample comprising a target analyte; and a detection zone present at another end of the lateral flow immunoassay device, downstream of the sample application zone for detecting the target analyte, wherein the detection zone comprises one or more first antibodies immobilized on a porous nitrocellulose membrane modified via a polymer covalently grafted on the porous nitrocellulose membrane, wherein the polymer is not a copolymer, and comprises a structural unit having a formula:

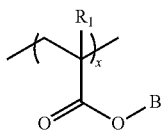

wherein (i) $R_1$ is H or $CH_3$, (ii) x is a number of repeat units and x is at least 2, (iii) a grafting level of the

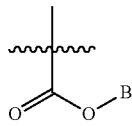

moiety is at least 300 μmol per gram of the porous nitrocellulose membrane, and (iv) B is:

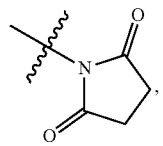

and a grafting level for the

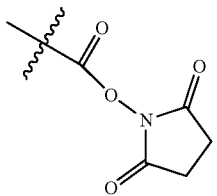 [SMILES: *C(=O)ON1C(=O)CCC1=O]

moiety of the polymer in the porous nitrocellulose membrane is less than 350 μmol of the

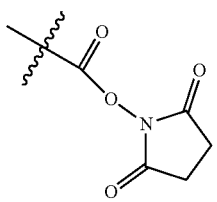 [SMILES: *C(=O)ON1C(=O)CCC1=O]

moiety per gram of the porous nitrocellulose membrane; and wherein the lateral flow immunoassay device is configured to flow the biological sample along a length of the lateral flow immunoassay device from the sample application zone to the detection zone.

2. The lateral flow immunoassay device of claim 1, wherein $R^1$ is H.

3. The lateral flow immunoassay device of claim 1, wherein the device further comprises a second polymer covalently grafted on the porous nitrocellulose membrane, the second polymer comprising a structural unit having a formula:

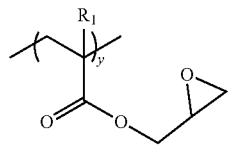

wherein $R^1$ is H or $CH_3$, and y is a number of repeat units and is at least 2.

4. The lateral flow immunoassay device of claim 1, further comprising one or more detection probes coupled to the target analyte, wherein the target analyte is bound to the antibodies immobilized on the modified porous membrane.

5. The lateral flow immunoassay device of claim 4, wherein the one or more detection probes comprise an enzyme, a fluorescent dye, a luminescent material, a bioluminescent material, a radioactive material, a gold particle, a polymeric particle containing an optical reporter, or combinations thereof.

6. The lateral flow immunoassay device of claim 1, wherein the sample application zone further comprises a sample pad.

7. The lateral flow immunoassay device of claim 1, wherein the sample application zone further comprises a purification membrane for purification of the target analyte.

8. The lateral flow immunoassay device of claim 1, further comprising a conjugate release pad between the sample application zone and the detection zone.

9. The lateral flow immunoassay device of claim 1, further comprising a wicking pad.

10. The lateral flow immunoassay device of claim 1, wherein the detection zone further comprises a control line and a test line, wherein the test line comprises the antibodies.

11. The lateral flow immunoassay device of claim 1, further comprising a solid support, wherein the solid support is selected from a microtiter plate, petri plate, or a glass slide.

12. The lateral flow immunoassay device of claim 1, wherein the biological sample is blood, serum, lymph, urine, saliva, mucus, bodily secretions, cells, or tissue.

13. A lateral flow immunoassay device comprising:
a sample application zone at one end of the lateral flow immunoassay device for applying a biological sample comprising a target analyte; and
a detection zone present at another end of the lateral flow immunoassay device, downstream of the sample application zone for detecting the target analyte, wherein the detection zone comprises one or more antibodies immobilized on a porous nitrocellulose membrane modified via a polymer covalently grafted on the porous nitrocellulose membrane, wherein the polymer is not a copolymer, and comprises a structural unit having a formula:

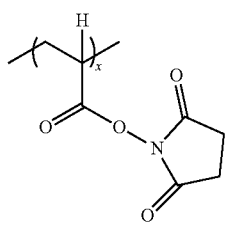

wherein x is at least 2 and is a number of repeat units and a grafting level for the

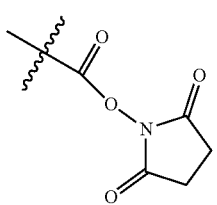

moiety of the polymer in the modified porous nitrocellulose membrane is at least 300 µmol and less than 350 µmol of the

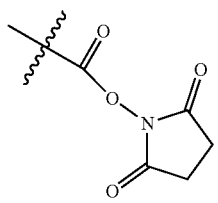 [SMILES: *C(=O)ON1C(=O)CCC1=O]

moiety per gram of the modified porous nitrocellulose membrane; and wherein the lateral flow immunoassay device is configured to flow the biological sample along a length of the lateral flow immunoassay device from the sample application zone to the detection zone and the target analyte is detected by binding to the antibodies.

\* \* \* \* \*